United States Patent
Lawton, Jr.

(10) Patent No.: US 9,487,565 B2
(45) Date of Patent: *Nov. 8, 2016

(54) ZEIN COMPOSITION AND METHODS OF PRODUCTION

(71) Applicant: Poet Research, Inc., Sioux Falls, SD (US)

(72) Inventor: John W. Lawton, Jr., Sioux Falls, SD (US)

(73) Assignee: Poet Research, Inc., Sioux Falls, SD (US)

(*) Notice: Subject to any disclaimer, the term of this patent is extended or adjusted under 35 U.S.C. 154(b) by 0 days.

This patent is subject to a terminal disclaimer.

(21) Appl. No.: 14/285,416

(22) Filed: May 22, 2014

(65) Prior Publication Data

US 2014/0303348 A1 Oct. 9, 2014

Related U.S. Application Data

(63) Continuation of application No. 12/965,255, filed on Dec. 10, 2010, now Pat. No. 8,795,760, which is a continuation-in-part of application No. PCT/US2009/069969, filed on Dec. 31, 2009.

(60) Provisional application No. 61/196,720, filed on Dec. 31, 2008, provisional application No. 61/207,868, filed on Dec. 31, 2008, provisional application No. 61/161,313, filed on Mar. 18, 2009, provisional application No. 61/161,318, filed on Mar. 18, 2009, provisional application No. 61/161,322, filed on Mar. 18, 2009, provisional application No. 61/161,325, filed on Mar. 18, 2009.

(51) Int. Cl.
*C07K 14/425* (2006.01)
*C12P 7/06* (2006.01)

(52) U.S. Cl.
CPC ........... *C07K 14/425* (2013.01); *C12P 7/06* (2013.01); *Y02E 50/16* (2013.01); *Y02E 50/17* (2013.01)

(58) Field of Classification Search
CPC ................. C07K 14/425; C12P 7/06
See application file for complete search history.

(56) References Cited

U.S. PATENT DOCUMENTS

| | | | |
|---|---|---|---|
| 2,132,250 | A | 10/1938 | Wagner |
| 4,309,254 | A | 1/1982 | Dahlstrom et al. |
| 4,617,270 | A | 10/1986 | Anderson et al. |
| 4,857,279 | A | 8/1989 | Kawamata et al. |
| 5,250,182 | A | 10/1993 | Bento et al. |
| 5,510,463 | A | 4/1996 | Takahashi et al. |
| 5,620,728 | A | 4/1997 | Langley et al. |
| 6,755,975 | B2 | 6/2004 | Vane et al. |

(Continued)

FOREIGN PATENT DOCUMENTS

| | | |
|---|---|---|
| JP | 60-106820 | 6/1985 |
| WO | WO-2010/075541 A2 | 7/2010 |

OTHER PUBLICATIONS

Lawton, J., "Isolation of Zein Using 100% Ethanol"—Cereal Chem. 2006, 83(5), 565-568.*

(Continued)

*Primary Examiner* — Elizabeth Gwartney
(74) *Attorney, Agent, or Firm* — Foley & Lardner LLP

(57) ABSTRACT

A high cysteine content zein composition is provided. A method and system for the manufacture of the bioproduct is likewise disclosed herein.

25 Claims, 18 Drawing Sheets

(56) References Cited

U.S. PATENT DOCUMENTS

| | | |
|---|---|---|
| 7,122,709 B2 | 10/2006 | Fanselow et al. |
| 7,297,236 B1 | 11/2007 | Vander Griend |
| 7,452,425 B1 | 11/2008 | Langhauser |
| 8,652,818 B2 | 2/2014 | Lawton et al. |
| 2004/0009263 A1 | 1/2004 | Liu et al. |
| 2004/0234649 A1 | 11/2004 | Lewis et al. |
| 2005/0101700 A1 | 5/2005 | Riebel |
| 2005/0233030 A1 | 10/2005 | Lewis et al. |
| 2005/0239181 A1 | 10/2005 | Lewis et al. |
| 2007/0031954 A1 | 2/2007 | Mairal et al. |
| 2007/0037267 A1 | 2/2007 | Lewis et al. |
| 2007/0178567 A1 | 8/2007 | Lewis |
| 2007/0196907 A1 | 8/2007 | Lewis |
| 2007/0202214 A1 | 8/2007 | Lewis et al. |
| 2008/0176298 A1 | 7/2008 | Randhava et al. |
| 2008/0213429 A1 | 9/2008 | Binder et al. |
| 2009/0181153 A1 | 7/2009 | Bendorf et al. |
| 2010/0159071 A1 | 6/2010 | Redford |
| 2010/0159514 A1 | 6/2010 | Redford |
| 2010/0159548 A1 | 6/2010 | Redford |
| 2010/0159549 A1 | 6/2010 | Redford |
| 2010/0159550 A1 | 6/2010 | Redford |
| 2010/0159551 A1 | 6/2010 | Redford |
| 2011/0111085 A1 | 5/2011 | Lewis et al. |
| 2011/0143013 A1 | 6/2011 | Lawton, Jr. |

OTHER PUBLICATIONS

Parris et al., "Extraction and Solubility Characteristics of Zein Proteins from Dry-Milled Corn"—J. Agric. Food Chem. 2001, 49, 3757-3760.*

Ayers, "The 'Can Do' Review", Todd & Sargent Inc., Jan. 2007, 31(1), 8 pages.

Cookman et al., "Extraction of protein from distiller's grain", Biosource Technology, 100 (2009) 2012-2017.

Egorova et al., "Different Methods for Preparing a Feed Meal from Fresh and Acid-Preserved Fish Scraps", Tr. Vses. Nauchno.-Issled. Inst. Morsk. Rybn. Khoz. i Okeanogr (Proceedings of the All-Union Research Institute of Marine Fisheries and Oceanography), 1962, vol. 45, pp. 134-138 (CA English Abstract only).

Jacela et al., "Amino acid digestibility and energy content of corn distillers meal for swine", Available online at www.asi.ksu.edu on Oct. 24, 2007.

Lawton, "Isolation of Zein Using 10% Ethanol Cereal Chem." 83(5):565-568, 2006.

Liu et al., "Thermal Degradation and Stability of Starch Under Different Processing Conditions," Starch, (2013), 65: 48-60.

Liu et al., "Thermal-Oxidative Degradation of High-amylose Corn Starch," J. Them. Anal. Calorim., (2014), 115:659-665.

McKenna, "Ethanol helps a small town bloom", Toronto Globe and Mail, Jul. 25, 2007, cited in Scrippsnews URL:http://www.scrippsnews.com/node/25654, 3 pages.

Mustakas, "Recovery of oil from soybeans", USDA NRRC-ARSEA, in Handbook of Soy Oil Processing and Utilization, Am. Soybean Assn. and Am. Oil Chemists; Soc., 1980, Chapter 4, pp. 49-65.

Parris, et al., "Extraction and Solubility Characteristics of Zein Proteins from Dry-Milled Corn," J. Agric. Food Chem., (2001), 49:3757-3760.

US-EPA, "Draft regulatory impact analysis: Changes to renewable fuel standard program", EPA-420-D-09-001, May 2009, 822 pages.

Wakeman, "Extraction, Liquid-solid", Kirk-Othmer Encyclopedia of Chemical Technology, Dec. 4, 2000, pp. 1-14.

Widyaratne, et al., "Nutritional Value of Wheat and Corn Distillers Dried Grain With Solubles: Digestibility and Digestible Contents of Energy, Amino Acids and Phosphorous, Nutrient Excretion and Growth Performance of Grower-Finisher Pigs," Canadian Journal of Animal Science, (2007), 103-114.

Winowiski, "Pellet quality in animal feeds", Available online at www.adiveter.com on Jan. 31, 2001.

Wolf et al., "Isolation and Characterization of Zein from Corn Distillers' Grains and Related Fractions." Cereal Chem, 74(5):530-536, 1997.

Wu et al., "Evaluation of corn distillers' dried grains defatted with supercritical carbon dioxide", Cereal Chem. 1990, 67(6), pp. 585-588.

Lawton, et al., Zein Recovery from Coproducts of a Raw Starch Fermentation Bioethanol Process, Seventh International Starch Technology Conference, University of Illinois at Urbana-Champaign, Jun. 5-8, 2001.

Lawton, Proteins of the Kernel, Ch. 9,Chemistry and Technology, (2003), pp. 313-354.

\* cited by examiner

| CONVENTIONAL FERMENTATION | | | as is | dry |
|---|---|---|---|---|
| | Ethanol | pH | Solids | Protein | Protein |
| Average | 19.4 | 4.09 | 12.8 | 4.40 | 34.4 |
| Experiment 1 & 2 | 20.0 | 4.03 | 12.9 | 4.3 | 33.4 |

| RAW STARCH FERMENTATION (706) | | | as is | dry |
|---|---|---|---|---|
| | Ethanol | pH | Solids | Protein | Protein |
| Average | 19.5 | 3.78 | 11.9 | 3.89 | 32.7 |
| Experiment 3 & 4 | 19.9 | 3.77 | 12.7 | 4.16 | 32.9 |

| ENDOSPERM FERMENTATION (708) | | | as is | dry |
|---|---|---|---|---|
| | Ethanol | pH | Solids | Protein | Protein |
| Average | 18.3 | 4.24 | 9.30 | 4.01 | 43.1 |
| Experiment 5 & 6 | 17.9 | 3.67 | 8.43 | 3.35 | 39.8 |

BEER COMPOSITION (percent)

FIGURE 7A

| RAW STARCH FERMENTATION | | |
|---|---|---|
| Moisture | Sulfur* | Protein* |
| 69.1 | 0.67 | 31.0 |

* Average composition, percent of dry matter

WET CAKE COMPOSITION (percent)

FIGURE 7B

| CONVENTIONAL FERMENTATION | | |
|---|---|---|
| Moisture | Sulfur* | Protein* |
| 9.40 | 0.83 | 27.9 |

| RAW STARCH FERMENTATION (716) | | |
|---|---|---|
| Moisture | Sulfur* | Protein* |
| 8.4 | 0.99 | 28.5 |

| ENDOSPERM FERMENTATION (718) | | |
|---|---|---|
| Moisture | Sulfur* | Protein* |
| 7.5 | 0.84 | 42.2 |

* Average composition, percent of dry matter

DRIED SOLIDS COMPOSITION (percent)

FIGURE 7C

| Zein Extraction Operating Conditions | | | |
|---|---|---|---|
| | Typical Range | Example 1 | Example 2 |
| Solvent to Solids Ratio | 4:1 – 10:1 | 4:1 – 7:1 | 5:1 |
| Solvent Ethanol Concentration | 40 – 90 percent | 50 – 80 percent | 60 – 70 percent |
| Sodium Hydroxide Concentration | 0 – 7.0 percent | 2.8 – 4.0 percent | 3.2 – 3.8 percent |
| Temperature | 20 – 78 degrees Celsius | 50 – 75 degrees Celsius | 68 – 70 degrees Celsius |
| Extraction Time | 20 – 120 minutes | 25 – 60 minutes | 28 – 30 minutes |

FIGURE 10

Zein Extraction Operating Conditions (1100)

Solvent to solids ratio (weight of solvent relative to weight of solids): (1102)

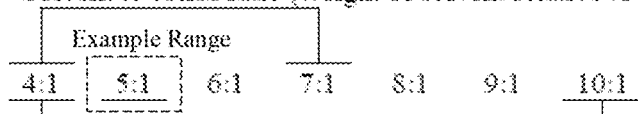

Solvent to solids concentration for zein extraction from beer: (1104)

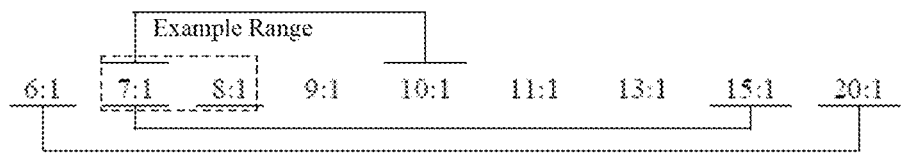

Solvent Ethanol Concentration (weight percent concentration of ethanol in extraction solvent): (1106)

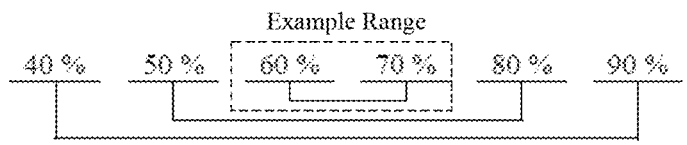

Sodium Hydroxide Concentration (weight percent of solids on a dry basis): (1108)

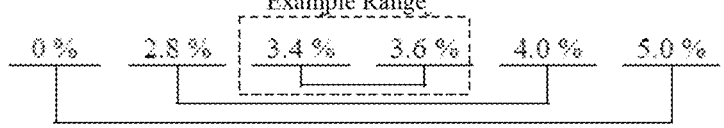

Extraction temperature (temperature of the slurry in the extraction vessel): (1110)

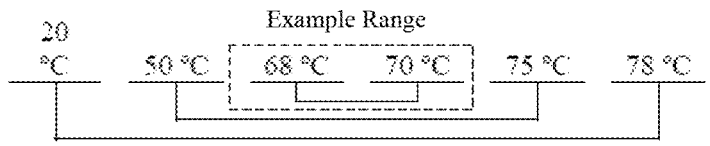

Extraction time (duration of time slurry is held at extraction temperature): (1112)

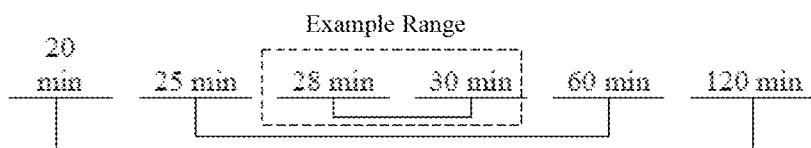

FIGURE 11

Zein Extraction Yield from Different Starting Materials

|  | Beer | Wet Cake | DDG |
|---|---|---|---|
| Conventional Fermentation | 4.71 g | 5.59 g | 3.21 g |
| Raw Starch Fermentation | 6.90 g | 5.91 g | 6.29 g |
| Endosperm Raw Starch Fermentation | 7.98 g | 8.24 g | 8.35 g |

Yield and Composition of Zein Extraction from Different Starting Materials

| Starting Material | NaOH* | Zein recovered (g) dry basis | Protein dry basis % | Fat dry basis % | α-zein content % | β and γ-zein content % |
|---|---|---|---|---|---|---|
| High Protein DDG | Yes | 9.05 | 91.0 | 1.5 | 77-88 | 12-23 |
| High Protein DDG | No | 5.7 | 86.5 | 7.0 | 100 | 0 |
| Per-extracted High Protein | Yes | 5.8 | 92.3 | 0.6 | 59 | 41 |
| Corn Gluten Meal | Yes | 13.4 | 96.8 | 1.8 | 97.1 | 2.87 |
| Corn Gluten Meal | No | 14.7 | 94.7 | 2.8 | 96.7 | 3.3 |
| Per-extracted CGM | Yes | 5.1 | 93.8 | 0.7 | 71.2 | 28.8 |

*Alkali Extraction Agent

ZEIN COMPOSITION AND METHODS OF PRODUCTION

CROSS-REFERENCE TO RELATED APPLICATIONS

The present application is a continuation of co-pending U.S. application Ser. No. 12/965,255, which is a continuation-in-part of International Application No. PCT/US2009/69969, filed Dec. 31, 2009, which claims priority to U.S. Provisional Patent Application Nos. 61/196,720, filed Dec. 31, 2008, U.S. Provisional Patent Application No. 61/207,868, filed Dec. 31, 2008, U.S. Provisional Patent Application No. 61/161,313, filed Mar. 18, 2009, U.S. Provisional Patent Application No. 61/161,318, filed Mar. 18, 2009; U.S. Provisional Patent Application No. 61/161,322, filed Mar. 18, 2009, and U.S. Provisional Patent Application No. 61/161,325, filed Mar. 18, 2009, each of which are incorporated herein by reference in their entirety.

GOVERNMENT INTERESTS

The Government may have rights in an invention claimed in the present application pursuant to Contract No. DE-FG36-08G08033 with the Department of Energy.

TECHNICAL FIELD

The present application relates to systems and methods for the extraction of protein from a fermentation product. The present application also relates to a system for the extraction of zein from fermented solids in the production of ethanol from corn. The present application further relates to a composition of extracted zein comprising alpha-zein, beta-zein, and gamma-zein.

BACKGROUND

Zein is a group of plant proteins that can be extracted from corn or corn-protein-containing substrates, such as corn gluten meal and has utility as a raw material for a variety of non-toxic and renewable polymer applications. Zein is classified as GRAS (Generally Recognized As Safe) by the U.S. Food and Drug Administration and has a variety of commercial uses including the manufacture of edible food packaging, edible films, biodegradable plastic resins, chewing gum base, tablet-coating compounds, adhesives, coatings for paper cups, soda bottle cap linings, etc. Zein can also be processed into resins and other bioplastic polymers, which can be extruded or rolled into a variety of plastic products.

Zein belongs to a class of proteins called prolamins, which are soluble in alcohol, and comprises approximately forty to fifty percent of the total protein in corn, or about four percent of the corn kernel. Zein has been further divided into four subclasses: alpha-zein, beta-zein, gamma-zein, and delta-zein. Alpha-zein is the primary commercially used zein and accounts for about seventy percent of the zein in corn. Beta-zein accounts for about five percent of the zein in corn. Gamma-zein accounts for approximately twenty to twenty-five percent of the zein in corn and delta-zein accounts for about one to five percent of the zein in corn. Each zein type (alpha, beta, gamma, and delta) has a different amino-acid profile and exhibits slightly different physical properties.

Zein can be extracted and recovered from corn or co-products from corn processing. The composition and characteristics of the resulting zein may depend on the starting material and the extraction solvent.

For example, ethanol can be produced from grain-based feedstocks (such as corn). Ethanol production from corn produces fermentation products (e.g., co-products) that are suitable for use as starting materials for zein extraction. One such co-product includes corn gluten meal (CGM), a by-product of wet milling ethanol production. In a typical wet milling process, ethanol is produced from corn by first steeping the corn kernels in water that contains sulfur dioxide, and then separating the kernels into endosperm, fiber and germ. The endosperm is further processed to produce starch and corn gluten, which can be dried into Corn Gluten Meal. Corn Gluten Meal is a typical starting material for zein extraction due to its high protein content (sixty percent or greater). However, the sulfur dioxide or other chemicals that may be used during the preparation (e.g., in a steeping process) of corn gluten meal may adversely affect zein quality.

Another co-product from which zein may be extracted comes from a dry-milling process. In a typical dry-milling process, a starch containing material, such as corn, is ground into flour and slurried with water and enzymes. The slurry may be cooked to liquefy the starch and to facilitate saccharification. Additional enzymes may be added to complete saccharification to break down the starch into simple sugars (e.g. glucose) that can be fermented using an ethanologen (e.g. yeast). The fermentation produces a fermentation product that comprises a liquid portion or component and a solids portion or component. The liquid portion comprises ethanol, water, and other soluble components. The residual solids comprise, for example proteins, fiber, oil, and other insoluble components.

The fermentation product comprising a liquid component and a solids component may be distilled to separate ethanol and whole stillage (e.g. wet solids or fermentation solids). Whole stillage comprises residual solids and water, and may be further separated into wet cake and thin stillage. Wet cake (wet solids) can be dried into meal such as dried distillers grains (DDG); thin stillage can be reduced to syrup and added to the wet cake or meal during the drying process to produce dried distillers grains with solubles (DDGS). Meal such as DDG and DDGS can be used as an animal feed product. The wet cake or dried meals (DDG and/or DDGS) may be used as a starting material for zein extraction.

According to an alternative process, for example as described in U.S. Patent Application Publication No. 2005/0239181 (which is hereby incorporated by reference in its entirety), starch may be converted into sugars and fermented in a raw-starch process without "cooking" or liquefaction. Heat damage to proteins and other components of the slurry may be avoided by using the raw-starch process. The resulting wet cake, DDG or DDGS from the raw starch process may likewise be used for zein extraction.

Further, a dry fractionation process that does not utilize sulfur dioxide may be used instead of wet milling to fractionate the corn into endosperm, fiber and germ. The amount of residual solids in the fermentation product can be reduced by fractionation and by eliminating fiber and germ, both low in starch, from fermentation. Endosperm is primarily comprised of starch and protein with small amounts of fiber and oil present. Zein is also concentrated in the endosperm; more than half of the endosperm protein may be comprised of zein. When endosperm is fermented, the residual solids comprise a high concentration of zein. The dried residual solids from endosperm fermentation are high in protein and result in a meal that is called "high protein dried distiller grains" (DDG HP). DDG HP is well suited as a starting material for zein extraction.

As previously noted, four different types of zein proteins are present in corn: alpha-zein, beta-zein, gamma-zein, and delta-zein. Each zein type has a different amino-acid profile and exhibits slightly different properties. The predominant commercially available zein sold in industry currently is comprised almost entirely of alpha-zein. The melt strength of this zein is low making it ineffective as a material for blown films. Films of commercial zein are brittle and weak compared to synthetic films. These physical properties are the result of alpha-zein containing only one cysteine, thus making it able to only form one disulfide bond. In contrast, beta-zein and gamma-zein contain greater number of cysteine amino acid bases, at 12 and 15 cysteine respectively. Thus, zein formulations with greater concentrations of beta- and gamma-zein may have higher melting temperatures and greater plasticity. This may enable zein products to be utilized in a wider range of applications, including blown films, and plastics of greater strength.

It would be advantageous to provide for systems and methods for extracting protein from a fermentation product which yields high levels of beta- and gamma-zein. It would also be advantageous to provide for a system for producing ethanol that facilitated the recovery of co-products, including high cysteine zein compositions, extracted from components of the fermentation product. Further, it would also be advantageous to provide for a zein composition with high cysteine for improved physical properties.

SUMMARY

To achieve the foregoing and in accordance with the present invention, a system and method of producing a zein composition is disclosed. In particular, a zein composition including high cysteine content is disclosed. The zein composition may include alpha-, beta- and gamma-zein. In some embodiments, the beta- and gamma-zein may comprise from about 12% to about 60% of the zein in the zein composition. In other embodiments, beta and gamma zein content may be higher, such as at least 25%, 35% and 40%.

The zein composition can be produced from a feedstock in a system configured to produce ethanol and distillers grains from a fermentation product. The method comprises the steps of processing the feedstock into a starch containing component and creating a slurry comprising the starch containing component. The method comprises the steps of preparing the starch containing component of the slurry into a fermentable component for fermentation and fermenting at least a portion of the fermentable component of the slurry into the fermentation product. The method comprises the steps of processing the fermentation product into zein compositions comprising the ethanol and the distillers dried grains and producing a zein composition comprising from about 12% to about 60% of the zein in the zein composition from the fermentation product.

Producing the zein composition can comprise extracting a first zein composition from the fermentation product using a solvent solution in a first vessel. The fermentation product may then be subjected to a second extraction, whereby a second solvent solution extracts a second zein composition. The second solvent solution may include an extraction agent to increase the levels of cysteine (higher beta- and gamma-zein content) within the second zein composition. Extraction agents may include acids, sulfites, thiols, and alkalis, such as sodium hydroxide.

DESCRIPTION OF THE DRAWINGS

In order that the present invention may be more clearly ascertained, some embodiments will now be described, by way of example, with reference to the accompanying drawings, in which:

FIG. 5A is a process flow for zein extraction using a milling process. FIG. 5B is a process flow for zein extraction using a fractionation process.

FIG. 6A is a process flow for zein extraction from raw starch endosperm beer. FIG. 6B is a process flow for zein extraction from wet cake.

FIGS. 7A through 7C are tables of the average composition of fermented solids, in accordance with some embodiments. FIG. 7A is a table of beer composition for conventional, raw starch, and endosperm fermentation. FIG. 7B is a table of a wet cake composition for raw starch fermentation. FIG. 7C is a table of dried solids (DDG) composition for conventional, raw starch, and endosperm fermentation.

FIG. 10 is a table for the operating conditions and parameters for a zein extraction vessel, in accordance with some embodiments.

FIG. 11 is a graphical representation of parameters and operating conditions for a zein extraction process, in accordance with some embodiments.

DETAILED DESCRIPTION

The present invention will now be described in detail with reference to several embodiments thereof as illustrated in the accompanying drawings. In the following description, numerous specific details are set forth in order to provide a thorough understanding of embodiments of the present invention. It will be apparent, however, to one skilled in the art, that embodiments may be practiced without some or all of these specific details. In other instances, well known process steps and/or structures have not been described in detail in order to not unnecessarily obscure the present invention. The features and advantages of embodiments may be better understood with reference to the drawings and discussions that follow.

The present invention relates to compositions, and systems and methods of manufacture for these compositions. Particularly, high cysteine containing zein formulations are disclosed. These zein compositions include higher ratios of beta (β) and gamma (γ) zein, which include 12 and 15 cysteine respectively. In contrast, alpha (α) zein, of which almost all commercially available zein is composed of, contains a single cysteine. Cysteine enables the zein molecules to form disulfide bonds. As a result, plastics and films made from predominantly alpha zein may have low melting temperatures, and tend to be brittle and weak, in comparison to compositions of zein with greater levels of bet-a and gamma-zein which may be substantially stronger, with higher melting temperatures. This potentially opens a much larger range of applications to these cysteine-rich zein formulations, including durable plastics and blown films, for example.

Figure 1:
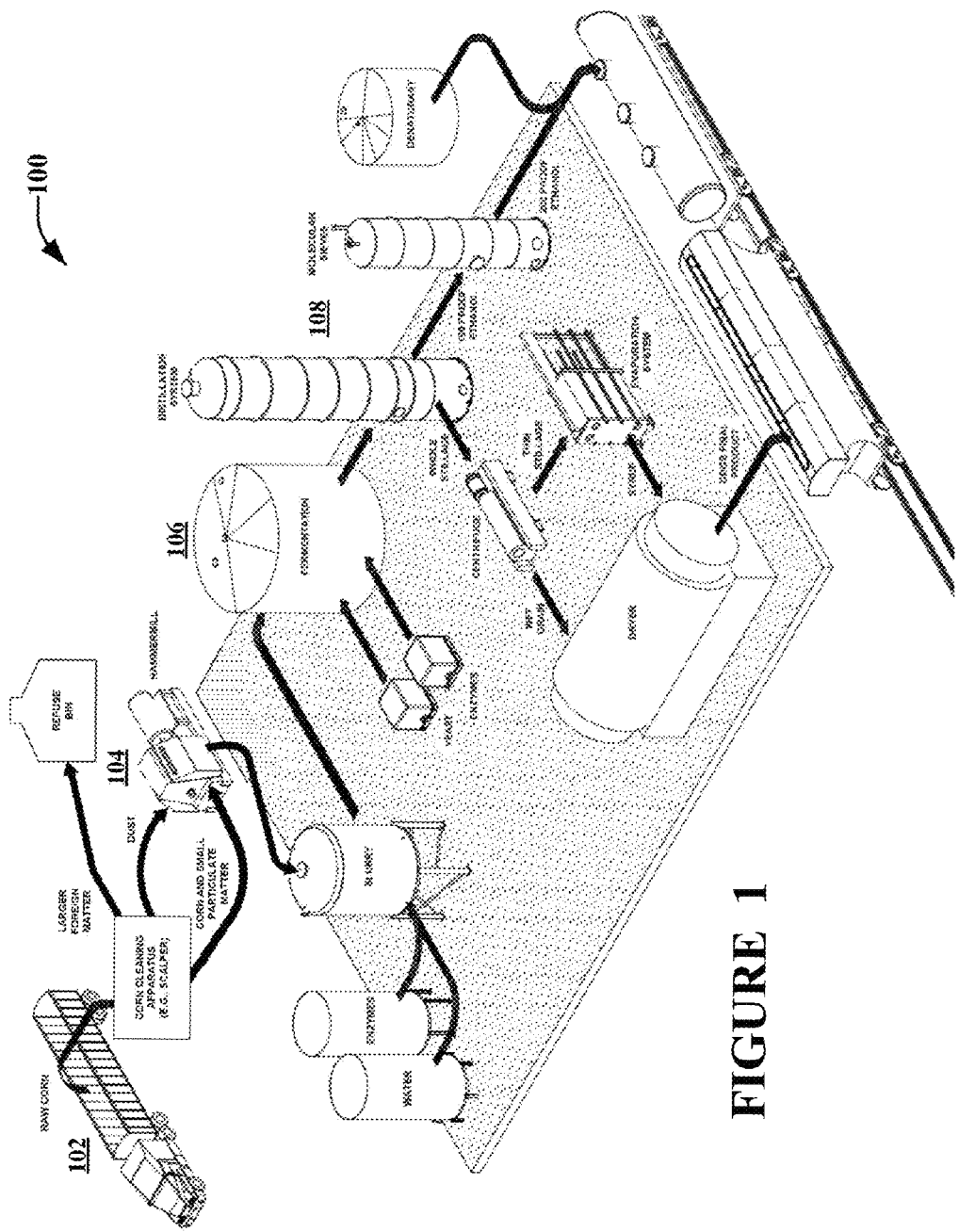
FIG. 1 is a diagram of an ethanol production facility, in accordance with some embodiments.

FIG. 1 is a schematic block diagram of an ethanol plant 100, in accordance with some embodiments. The ethanol plant can comprise a system configured to process feedstock into a fermentation product and zein compositions including ethanol and meal. The plant comprises a facility for producing corn-based ethanol and zein can be extracted from fermentation solids, a component of the fermentation product. The fermentation solids may comprise beer, beer solids, wet solids, wet cake, or dry solids, meal distillers grains, (e.g., DDG, DDGS, DDG HP). The ethanol plant can utilize various systems and methods, such as conventional starch liquefaction (e.g., cooked starch or raw starch hydrolysis, among other processes) to process corn (or other types of biomass).

The presently illustrated ethanol plant 100 includes an area 102 where corn (or other suitable material including, but not limited to, biomass, sugars, and other starch products) is delivered and prepared to be supplied to the ethanol production facility. The ethanol production facility comprises apparatus 104 for preparation and treatment (e.g., milling) of the corn into corn flour suitable for fermentation into fermentation product in a fermentation system 106. The ethanol production facility comprises a distillation system 108 in which the fermentation product is distilled and dehydrated into ethanol. The biorefinery may also comprise, in some embodiments, a by-product treatment system (shown as comprising a centrifuge, a dryer, and an evaporator).

Figure 2A:
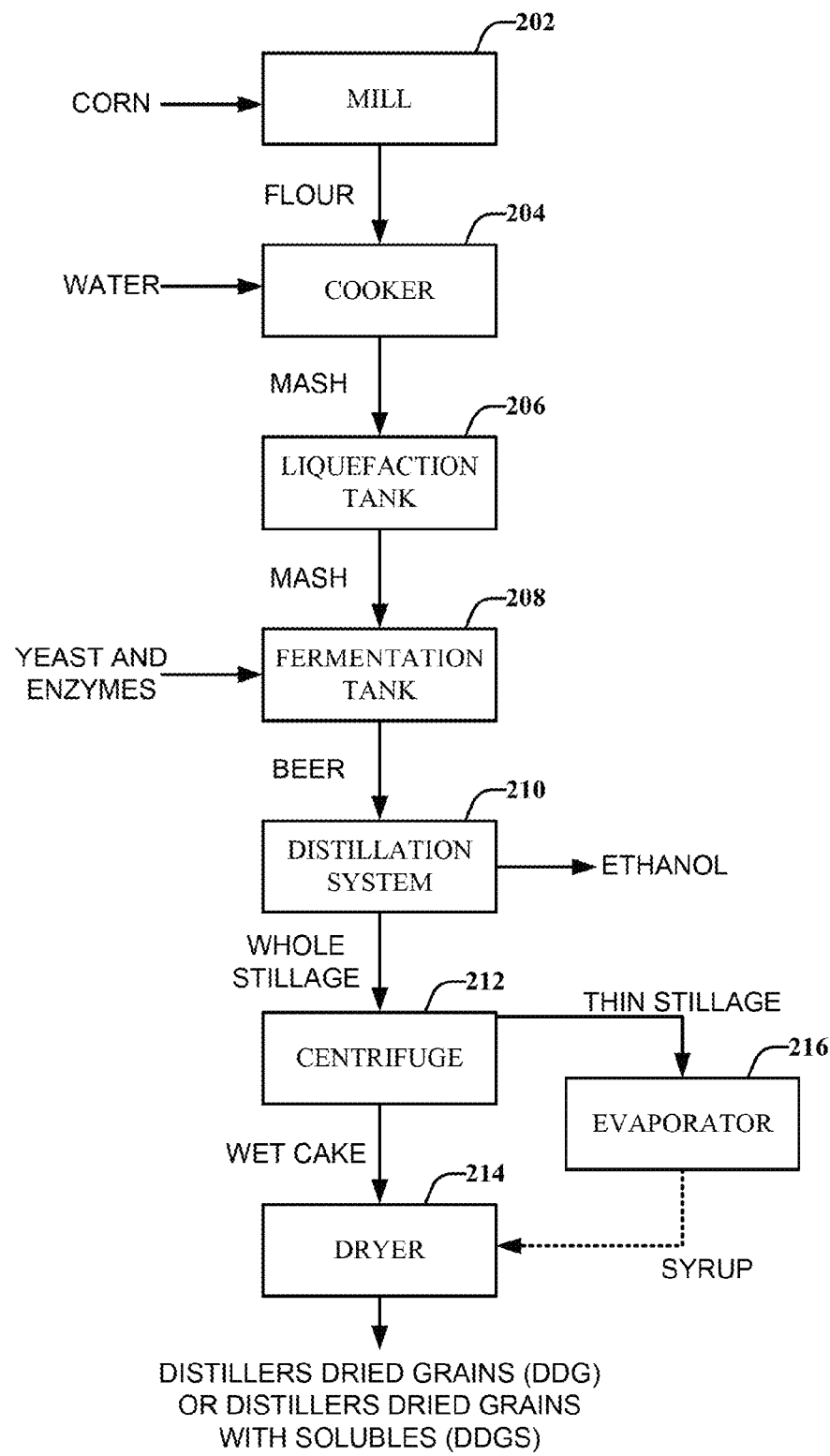
FIGS. 2A through 2C are block diagrams of an ethanol production facility, in accordance with some embodiments.
Figure 2B:
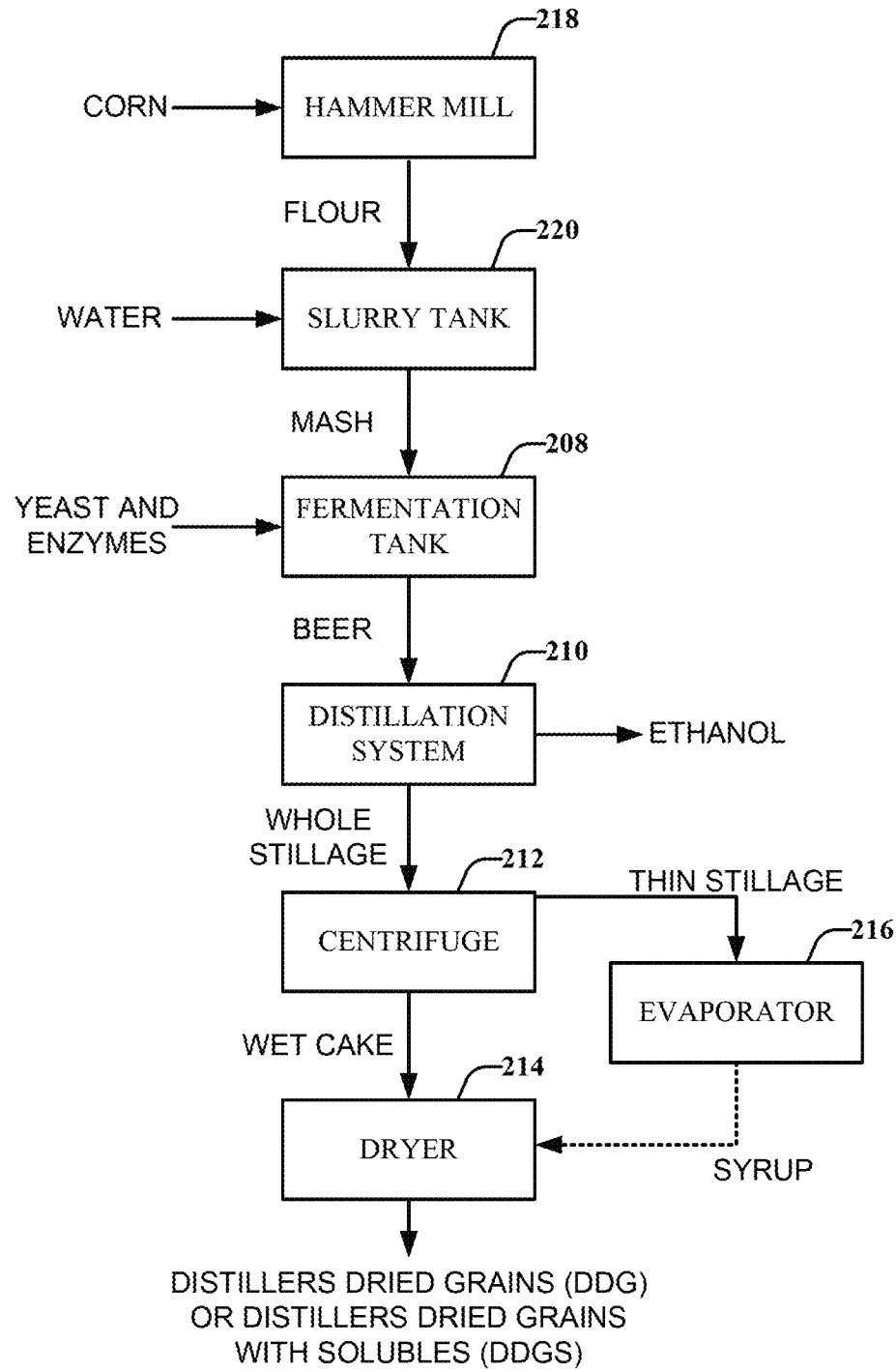
Figure 2C:
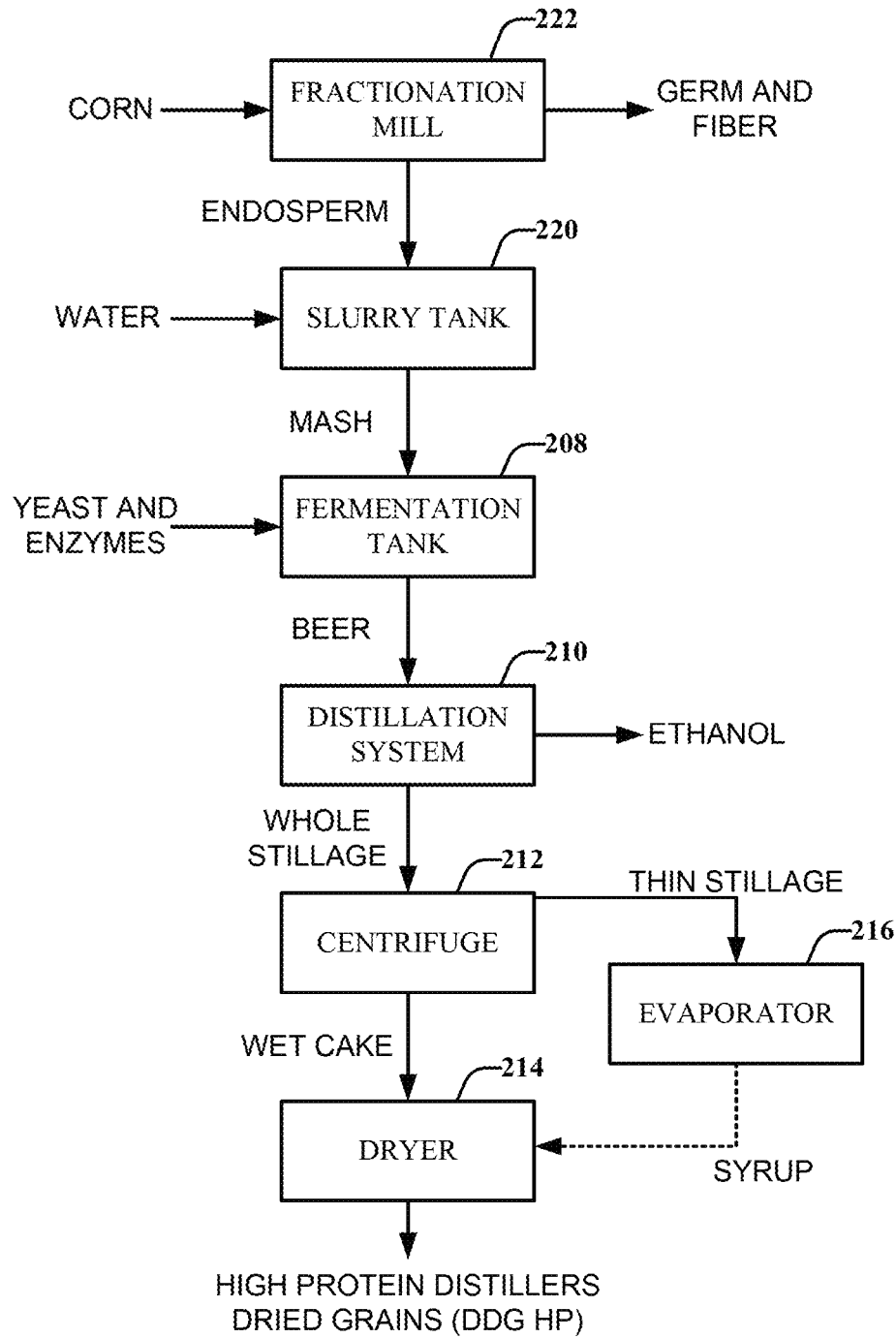

FIGS. 2A through 2C are schematic block diagrams of an ethanol production facility. FIG. 2A is a schematic block diagram of a system for a facility using a conventional "cooked starch" fermentation process 200. In a "cooked starch" ethanol plant producing ethanol from corn, corn kernels are processed by milling in a hammer mill 202 or other grinder in order to generate flour. The starch-containing flour is then slurried with water and cooked in a cooker 204 to generate mash. "Cooking" the slurry is typically performed at a temperature at or above the gelatinization temperature of the starch (typically at or above 60-75 deg C.). The mash may then be provided to a liquefaction tank 206 to be liquefied to facilitate saccharification where the starch is converted into sugar (glucose). The liquefied mash, plus enzymes and an ethanologen, may be provided to the fermentation tank 208 where the sugar is converted by the ethanologen (yeast) into ethanol. The product of the fermentation (fermentation product) is beer that comprises a liquid component and a solids component, which is provided to a distillation system 210 for separation of the ethanol. The leftover whole stillage may be separated by centrifuge 212 or screw press into wet cake (solids) or thin stillage (liquid). The thin stillage may be condensed in an evaporator 216 to syrup. Wet cake may be dried in the dryer 214 to yield dried distillers grain (DDG). The syrup may optionally be added to the DDG to yield dried distillers grain with solubles (DDGS).

FIG. 2B is a schematic block diagram of a system for a facility using a "raw starch" fermentation process. In "raw starch" fermentation, starch may be converted and fermented without "cooking" or liquefaction (as in the "cooked starch" process). In this system, the corm may be milled at a hammer mill 218, or other grinder, to flour. The flour may be added to a slurry tank 220 with water and enzymes to generate a mash. The mash may then be fermented as discussed above.

FIG. 2C is a schematic block diagram of a system for a facility using a raw starch endosperm fermentation process 204. In raw starch endosperm fermentation process, the corn kernel is fractionated in a fractionation mill 222 into endosperm, germ and fiber. The fractionation process is intended to separate the starch-containing endosperm from the germ and fiber (which are low in starch). The endosperm is then supplied to the slurry tank 220 of the "raw starch" fermentation process. For fractionated raw starch endosperm processing, the output after fermentation, distilling and drying is High Protein Dry Distillers Grain (DDG HP).

Figure 3:
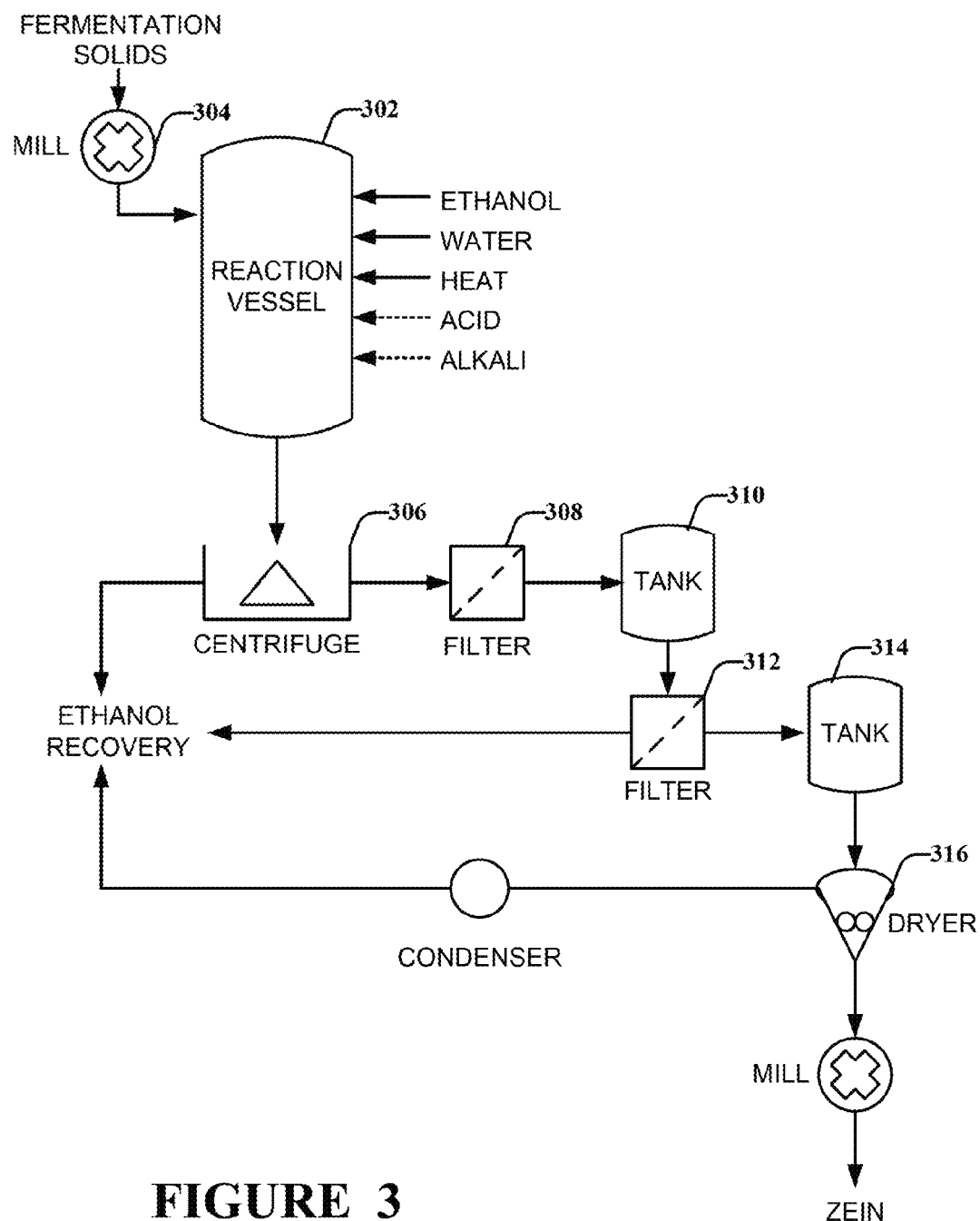
FIG. 3 is a first block diagram of the equipment used in an ethanol production facility comprising a system for extracting zein from fermented solids, in accordance with some embodiments.

One embodiment of the equipment used in an ethanol production facility for zein extraction from fermented solids (e.g., DDG HP, DDGS, DDG, beer, and wet cake) is illustrated in FIG. 3. Substantially the same equipment is utilized for each of the different fermentation processes (conventional, raw starch, raw starch endosperm) and for each of the different starting materials (Corn Gluten Meal, fermented solids, DDG HP, DDGS, DDG, beer, wet cake). According to an exemplary embodiment, the feedstock utilized is DDG HP. According to another embodiment, the feedstock used could be DDG. According to another embodiment, the feedstock used could be Corn Gluten Meal (CGM).

According to an exemplary embodiment, the zein extraction and recovery process may comprise three steps: extraction, refinement (e.g., purification), and recovery. The extraction step removes zein by solubilization; zein is soluble in aqueous alcohol. The extraction equipment comprises a reactor vessel 302 into which are input fermentation solids (which can be processed through a hammer mill 304); the fermentation solids are the output of the various ethanol processes shown in FIGS. 2A through 2C.

Other inputs to the reactor vessel 302 comprise an extraction agent (optional), alcohol, water, steam, and acid (optional). In this exemplary embodiment, the extraction agent utilized is Sodium Hydroxide (NaOH), however, in some embodiments other alkali or surfactants may be utilized as an extraction agent. In some embodiments the agent can comprise potassium hydroxide. In some embodiments the agent can comprise an acid, such as hydrochloric acid. The extraction agent can alternatively comprise an alkali hydroxide. In some embodiments the extraction agent can be sulfite, such as sodium metabisulfite. In some other embodiments the extraction agent can comprise a thiol, such as 2-mercaptoethanol.

According to certain embodiments, the alcohol can be selected from an alcohol composition comprising C1 to C7 alcohols (e.g., methanol, ethanol, or propanol). According to certain embodiments, the alcohol is ethanol.

According to an exemplary embodiment, the aqueous alcohol (or aqueous ethanol) solution comprises an extraction agent, such as sodium hydroxide in an amount based on the dry solids of the starting material. According to an exemplary embodiment, up to 7.0 percent of sodium hydroxide is used. According to some embodiment, the concentration of sodium hydroxide is 2.8-4.0 percent. According to some specific embodiment, the concentration of sodium hydroxide is 3.2-3.8 percent. Note that other alkali, detergents or surfactants may, in some embodiments, be likewise utilized as an extraction agent.

According to an embodiment, the contents of the reactor vessel 302 are drained into a centrifuge, such as a disc nozzle centrifuge 306 (or basket centrifuge), for separation into a solids component and a liquid component comprising ethanol and zein. Zein can be refined by filtration and recovered from the liquid component by drying or precipitation.

As illustrated, the refinement or purification step may comprise the use of multiple filters (or membranes) configured to remove matter having different sizes (e.g., membrane filters having different pore sizes). The first filter 308 can have, for example, one micrometer pore size (e.g., a micro filter). The first filter 308 is designed to protect the ultra filtration membrane by removing suspended solids that were not removed in the separation step. The solids are sent to a tank 310 and the liquids are further processed to recover the zein. The liquids are then passed over a second filter 312, which can be a membrane filter with a 10,000 molecular weight cutoff intended to remove small molecular weight components and to concentrate the zein solution. The retentate (e.g., zein/ethanol solution) is sent to a holding tank 314 (vessel or mixing reactor) and the permeate may be further processed for ethanol recovery (e.g., by distillation).

Zein is recovered from the retentate solution (e.g., from the second filter 312) by drying the solution (for example with a vacuum double drum dryer 316 or a desolventizer). In accordance with certain embodiments, the zein solution can be precipitated by diluting the alcohol concentration to where zein is no longer soluble (e.g., 50 percent (w/v) or less depending upon temperature).

In an embodiment, zeolite can be utilized to remove impurities from the zein composition. A crude solution of a zein contained in an aqueous alcohol solvent is contacted with a zeolite adsorbent under conditions effective for adsorption of the color and odor impurities in the zein solution onto the zeolite. The treated solution may be separated from the adsorbent with the intent to recover high quality zein dissolved in the aqueous alcohol solvent. Optionally, more impurities (e.g., residual color or order) can be removed by contacting the treated solution with an activated carbon adsorbent or a mixture of activated carbon and zeolite adsorbents. The process can be conducted using batch, semi-continuous, or continuous systems.

Figure 4:
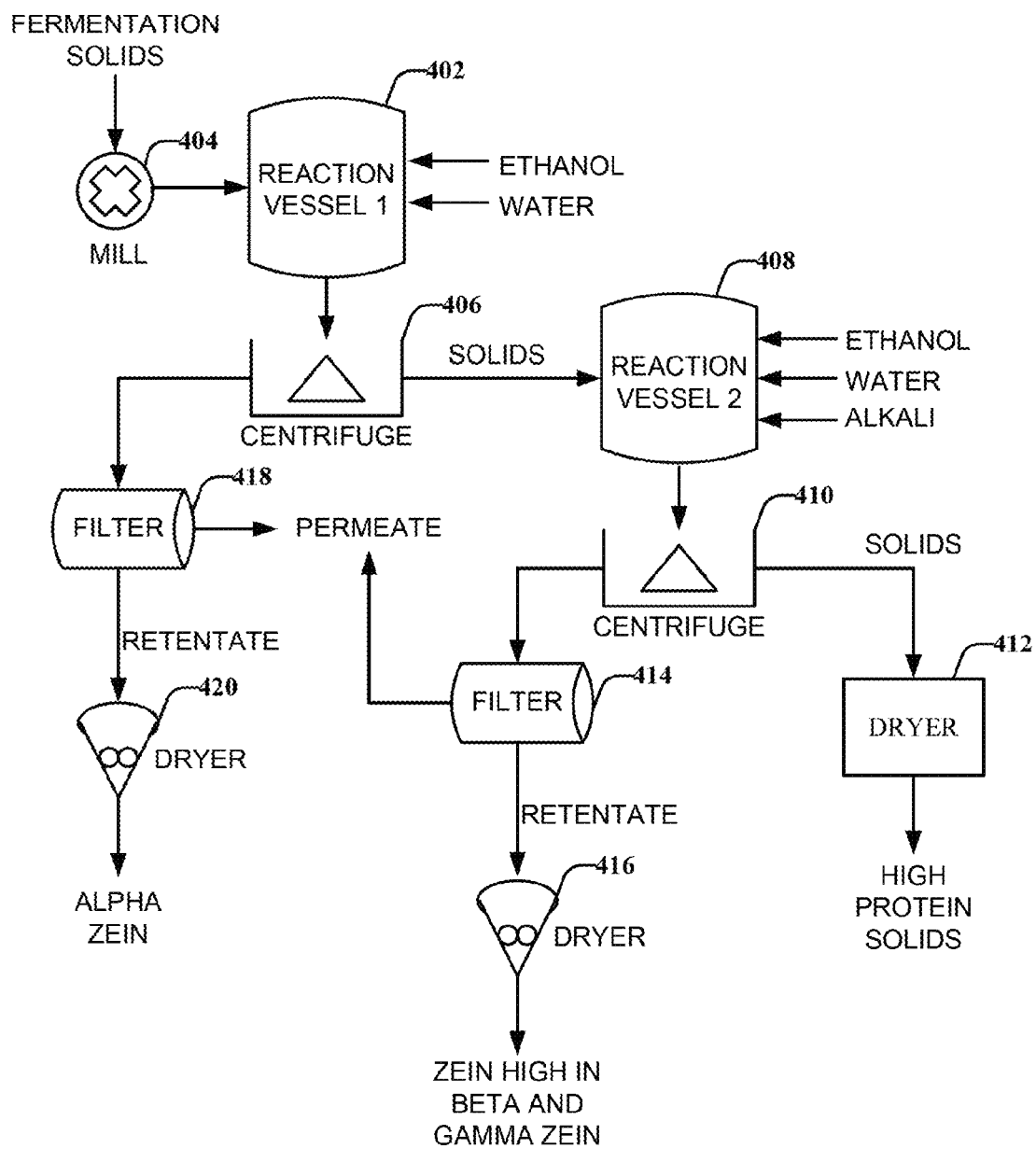
FIG. 4 is a second block diagram of the equipment used in an ethanol production facility comprising a system for extracting zein from fermented solids, in accordance with some embodiments.

Another embodiment of the equipment used in an ethanol production facility for zein extraction from fermented solids (e.g., DDG HP, DDGS, DDG, beer, and wet cake) is illustrated in FIG. 4. Such an extraction system may be utilized for the generation of high beta and gamma zein products. Substantially the same equipment is utilized for each of the different fermentation processes (conventional, raw starch, raw starch endosperm) and for each of the different starting materials (Corn Gluten Meal, fermented solids, DDG HP, DDGS, DDG, beer, wet cake). According to an exemplary embodiment, the feedstock utilized is DDG HP. According to another embodiment, the feedstock used could be DDG. According to another embodiment, the feedstock used could be Corn Gluten Meal (CGM).

According to an exemplary embodiment, the zein extraction and recovery process may comprise four steps: extraction, separation, re-extraction, refinement and recovery. The first extraction step removes primarily alpha zein by solubilization; zein is soluble in aqueous alcohol. The extraction equipment comprises a first reactor vessel 402 into which are input fermentation solids (which can be processed through a hammer mill 404); the fermentation solids are the output of the various ethanol processes shown in FIGS. 2A through 2C.

Other inputs to the first reactor vessel 402 comprise, alcohol, water, heat, and acid (optional). In this exemplary embodiment, the no extraction agent is utilized for the initial extraction. This ensures that the zein removed by initial extraction is predominantly alpha-zein. According to certain embodiments, the alcohol can be selected from an alcohol composition comprising C1 to C7 alcohols (e.g., methanol, ethanol, or propanol). According to certain embodiments, the alcohol is ethanol.

The mixture may be provided to a centrifuge 406 for separation of the liquids (including alpha zein, ethanol and water) from the solids (pre-extracted solids). The liquid portion may then be provided to one or more filters 418 for purification and concentration. The alpha zein may be recovered at a dryer 420 or via a precipitation. The permeate may be collected for ethanol recovery.

The pre-extracted solids, in this exemplary embodiment, may then be provided to a second reaction vessel for re-extraction of zein protein. Unlike the first extraction, however, and extraction agent is added to the second reaction vessel 408. According to an exemplary embodiment, the extraction agent may include an alkali, such as sodium hydroxide in an amount based on the dry solids of the starting material. According to an exemplary embodiment, up to 7.0 percent of sodium hydroxide is used. According to some embodiment, the concentration of sodium hydroxide is 2.8-4.0 percent. According to some specific embodiment, the concentration of sodium hydroxide is 3.2-3.8 percent. Note that other alkali, detergents or surfactants may, in some embodiments, be likewise utilized as an extraction agent.

According to an embodiment, the contents of the second reactor vessel 408 are drained into a centrifuge, such as a disc nozzle centrifuge 410 (or basket centrifuge), for separation into a solids component and a liquid component comprising ethanol and zein. Zein, with a high concentration of beta and gamma zein, can be refined by filtration and recovered from the liquid component by drying or precipitation. One or more filters 414 condense the high beta and gamma zein. Permeate from filtration may be collected for ethanol recovery and the like. The retentate, which includes the high beta- and gamma-zein, is provided to a dryer 416 (for example with a vacuum double drum dryer or a desolventizer) for recovery of the zein composition which is high in beta and gamma zein. In accordance with certain embodiments, the zein solution can be precipitated by diluting the alcohol concentration to where zein is no longer soluble (e.g., 50 percent (w/v) or less). Left over solids may also be dried in a dryer 412 to provide feed material, such as high protein DDG, Corn Gluten Meal, DDG or DDGS, dependent upon the starting material.

As with the previously disclosed system for zein extraction, in some embodiment, zeolite can be utilized to remove impurities from the zein composition. A crude solution of a zein contained in an aqueous alcohol solvent is contacted with a zeolite adsorbent under conditions effective for adsorption of the color and odor impurities in the zein solution onto the zeolite. The treated solution may be separated from the adsorbent with the intent to recover high quality zein dissolved in the aqueous alcohol solvent. Optionally, more impurities (e.g., residual color or order) can be removed by contacting the treated solution with an activated carbon adsorbent or a mixture of activated carbon and zeolite adsorbents. The process can be conducted using batch, semi-continuous, or continuous systems.

Figure 5A:
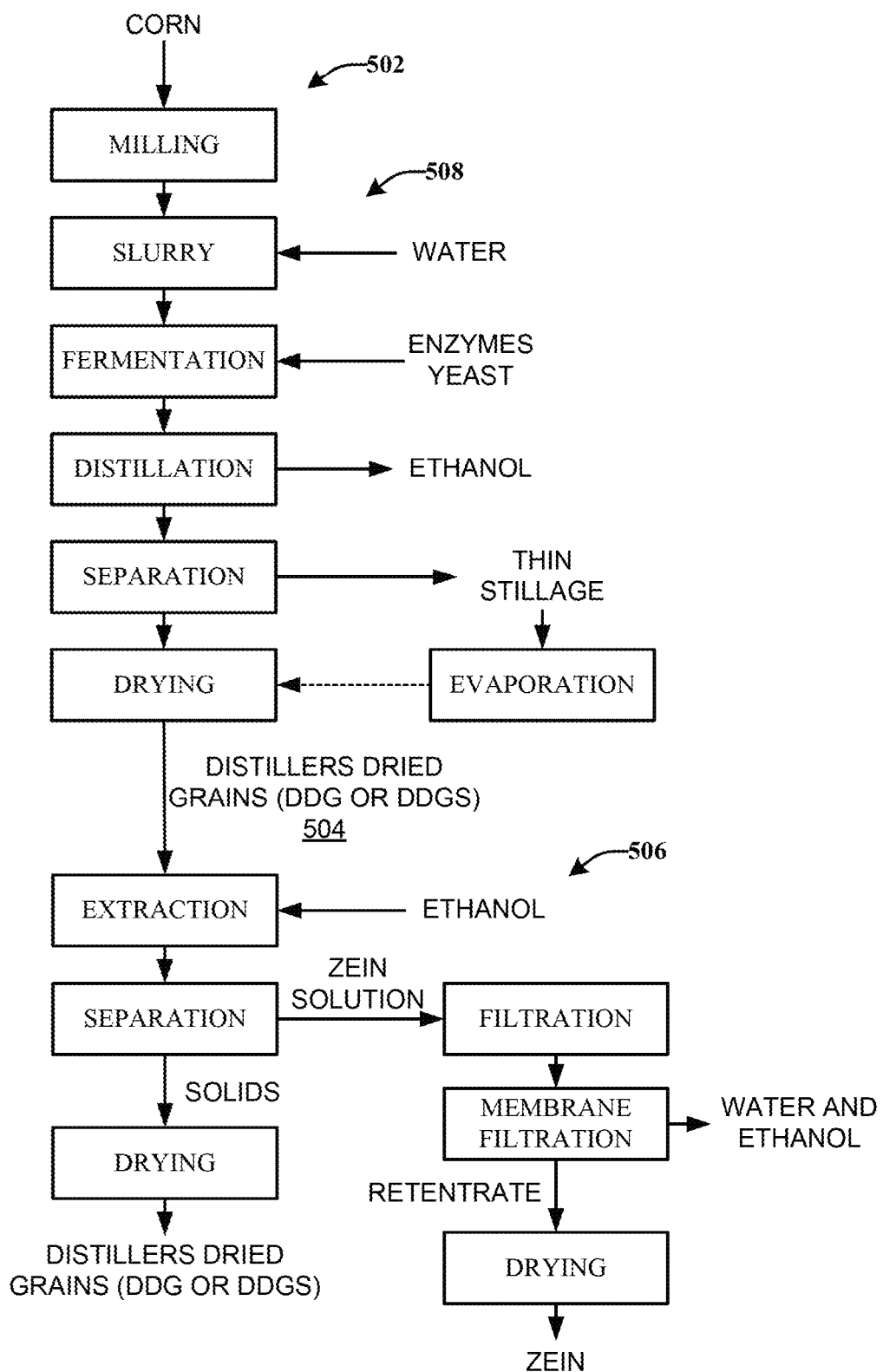
FIGS. 5A through 5B are process flow diagrams of a system for extraction of zein from raw starch dry solids (DDG) and raw starch endosperm dry solids (DDG HP), in accordance with some embodiments.
Figure 5B:
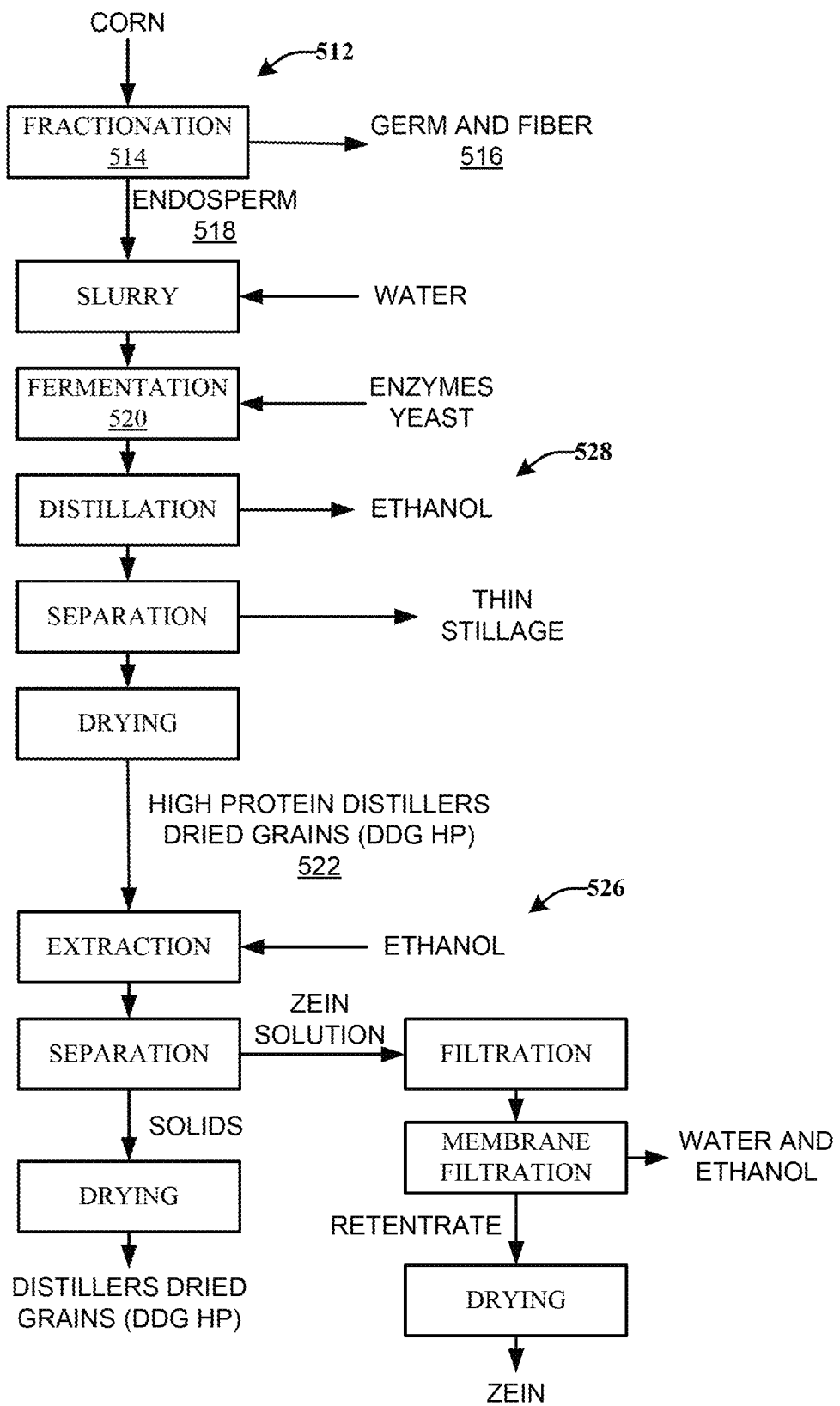

FIGS. 5A through 5B illustrate process flow diagrams for zein extraction from dry solids (DDG) and endosperm dry solids (DDG HP) from a raw starch fermentation process. FIG. 5A illustrates a process flow 502 for zein extraction from a raw starch fermentation process (e.g., without using fractionation). The DDG or DDGS 504 is used for zein extraction and recovery 506 can come from the ethanol production process 508 after the drying step 510. Zein extraction may include either of the single extraction, as outlined in FIG. 3, or the double extraction, as outlined in FIG. 4. A single extraction without an extraction agent yields a high alpha zein product. A single extraction with the extraction agent will provide a majority alpha zein with beta and gamma zein product. Double extraction yields two distinct products: an alpha zein product, and a high beta and gamma zein product. FIG. 5B illustrates a process flow 512 for zein extraction with fractionation 514. During fractionation 514, the corn germ and fiber 516 are separated from the endosperm 518 and removed, leaving the endosperm 518 for fermentation 520. The DDG HP 522 is used for zein extraction 526 and recovery after drying in the ethanol production process 528. Again, zein extraction may be either a single extraction or a double extraction dependent upon zein characteristics desired.

Figure 6A:
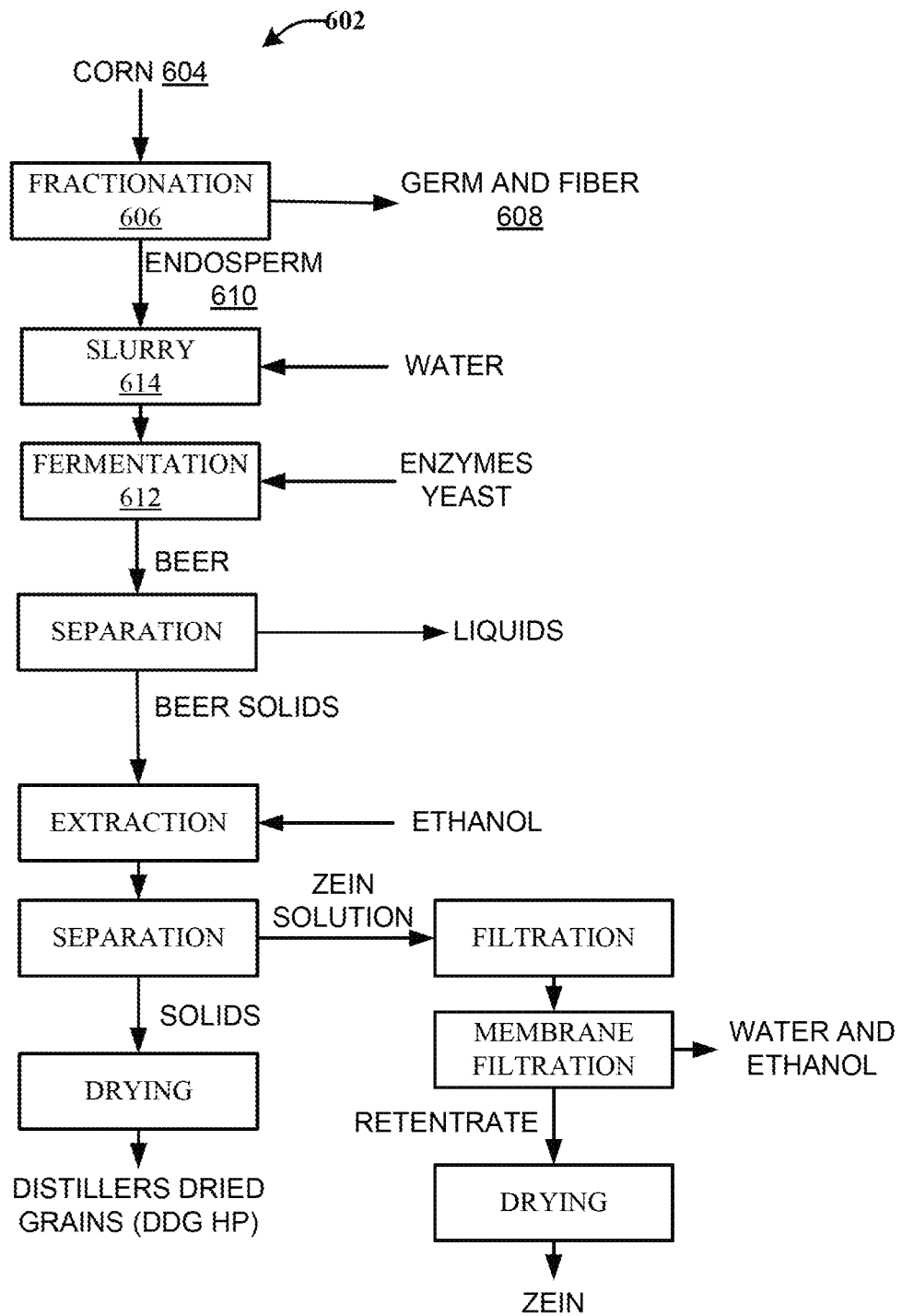
FIGS. 6A through 6B are process flow diagrams of a system for zein extraction, in accordance with some embodiments.
Figure 6B:
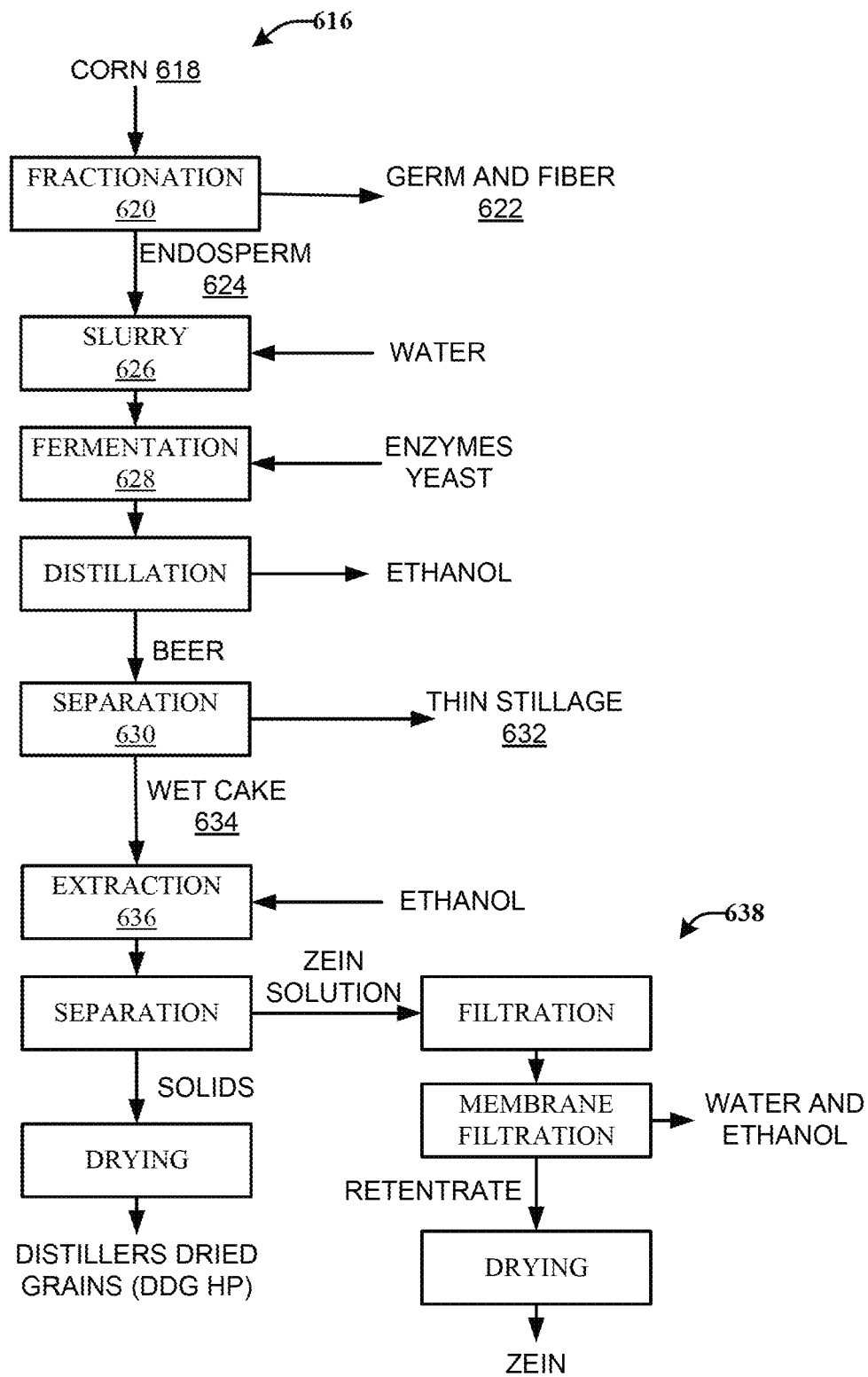

FIG. 6A illustrates a process flow 602 for zein extraction from raw starch endosperm beer. In this case, the corn 604 is fractionated 606 to remove the germ and fiber 608, leaving the endosperm 610 for fermentation 612. A slurry 614 is created. The beer solids are used for zein extraction and recovery after fermentation. Again, either a single or double extraction may be performed. FIG. 6B illustrates a process flow 616 zein extraction from wet cake. As illustrated, the corn kernel 618 undergoes fractionation 620 to remove the germ and fiber 622 from the endosperm 624. A slurry 626 is created. The endosperm 624 is saccharified and fermented 628 into a fermentation product, such as beer that is separated 630 into a liquid component, shown as thin stillage 632, and a solids component, shown as comprising wet cake 634. The wet cake 634 is used for zein extraction (either single or double extractions) 636 and recovery 638.

FIGS. 7A through 7C are tables of the average (representative for commercial production) composition of fermented solids (DDG, DDG HP, DDGS, beer, and wet cake), intended to be utilized as starting materials for zein extraction.

Figure 8:
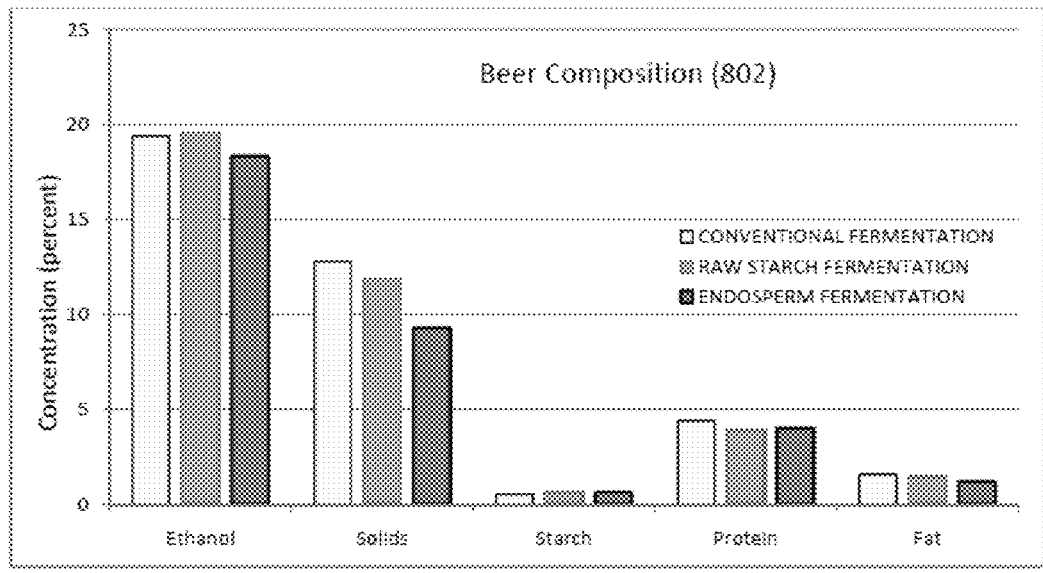
FIG. 8 is a chart for the average composition of beer in conventional, raw starch, and raw starch endosperm fermentations, in accordance with some embodiments.

FIG. 7A is a table of beer composition and is also visually represented in FIG. 8, which illustrates a chart for the average composition of beer used in examples according to an exemplary embodiment. Data for beer from three different types of processes is displayed: conventional fermentation, raw starch fermentation, and endosperm fermentation. The numbers are on an "as is" condition. The beer composition and other information was collected from six experiments.

Wet cake composition for raw starch fermentation is illustrated in FIG. 7B. The average moisture content of the wet cake is about 69 percent and protein content is about 31 percent of dry matter.

FIG. 7C illustrates a table for dried solids (DDG) composition for conventional fermentation, raw starch fermentation, and endosperm fermentation. The sulfur content and protein content illustrated are the average composition as a percent of dry matter.

Figure 9:
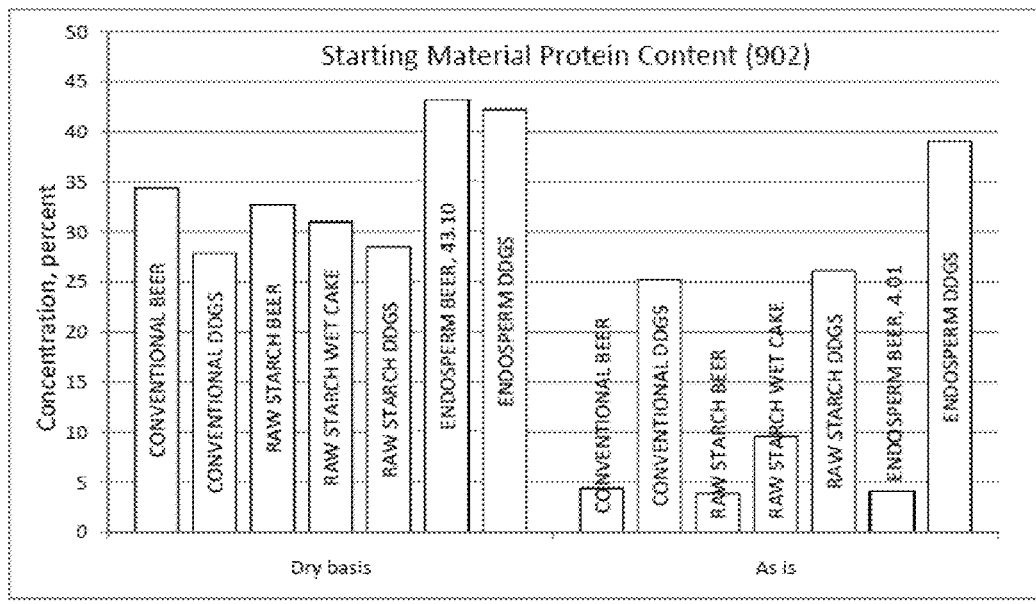
FIG. 9 is a chart for the average protein content in starting materials for zein extraction, in accordance with some embodiments.

A chart for the average protein content 902 in starting materials for zein extraction is illustrated in FIG. 9. The protein content for each starting material is divided into two subsets, one for dry basis (left portion of the chart) and one for the starting material in an "as is" condition (right portion of the chart). As illustrated, the starting material can be conventional beer, conventional DDGS, raw starch beer, raw starch wet cake, raw starch DDGS, endosperm beer, and/or endosperm DDGS. The concentration values are represented as percentages.

FIG. 10 illustrates a table for the operating conditions and parameters for a zein extraction. A typical range, an example range, and a second example value or range is provided for each of a solvent to solids ratio, a solvent to solids ratio for beer, a solvent ethanol concentration, a sodium hydroxide concentration, a temperature, and an extraction time. A graphical representation of these parameters and operating conditions is illustrated in FIG. 11. The ranges of zein extraction parameters and operating conditions are shown using nested ranges. The typical range is represented by the outer identified values, the first example range is identified by the inner identified values, and the second example value or range is identified within the dotted blocks.

The solvent to solids ratio 1102 is the weight of the solvent (combined ethanol and water) relative to the weight of the solids. A typical range of solvent to solids ratio is from 4:1 to 10:1. In one embodiment, the range of solvent to solids ratio is from 4:1 through to 7:1. In another embodiment, the solvent to solids ratio is 5:1.

For zein extraction from beer 1104, a typical range of solvent to solids ratio is from 6:1 to 10:1. In one embodiment, the range of solvent to solids ratio is from 7:1 to 10:1. In another embodiment, the solvent to solids ratio is from 7:1 to 8:1.

The solvent ethanol concentration 1106 is the weight percent concentration of ethanol in extraction solvent. A typical range for solvent ethanol concentration is from about 40 to about 90 percent. A first example range for solvent ethanol concentration is about 50 to about 80 percent. A second example range for solvent ethanol concentration is from about 60 to about 70 percent.

When an extraction agent is desired (e.g. for single extractions, and the re-extraction of double extractions) an alkali, detergent or surfactant may be used. In some cases sodium hydroxide may be a suitable extraction agent. The sodium hydroxide concentration 1108 is the weight of solids on a dry basis. A typical range for sodium hydroxide concentration is from 0 percent to about 5 percent. In one embodiment, the range is from about 2.8 percent to about 4.0 percent. In another embodiment, the range is 3.4 percent through 3.6 percent.

The extraction temperature 1110 is the temperature of the slurry in the extraction vessel. The temperature range for the zein extraction typically ranges from about 20 to about 78 degrees Celsius. In one embodiment, the temperature range for zein extraction is from about 50 to about 75 degrees Celsius. In another embodiment, the temperature range for zein extraction is from about 68 to about 70 degrees Celsius.

The extraction time 1112 is the duration of time the slurry is held at the extraction temperature. The extraction time typically ranges from about 20 to about 120 minutes. In one embodiment, the extraction time is from about 25 to about 60 minutes. In another embodiment, the extraction time is from about 28 to about 30 minutes.

EXAMPLES

A series of limited examples were conducted according to an exemplary embodiment of the system (as shown in FIGS. 3 and 4) in an effort to determine suitable apparatus and operating conditions for the manufacture of zein compositions and products. Experiments and tests were conducted to evaluate the zein compositions and yields from different starting materials and processes. The following example is intended to provide clarity to some embodiments of systems and means of operation and is not intended to limit the scope of the invention.

Figures 12, 13:
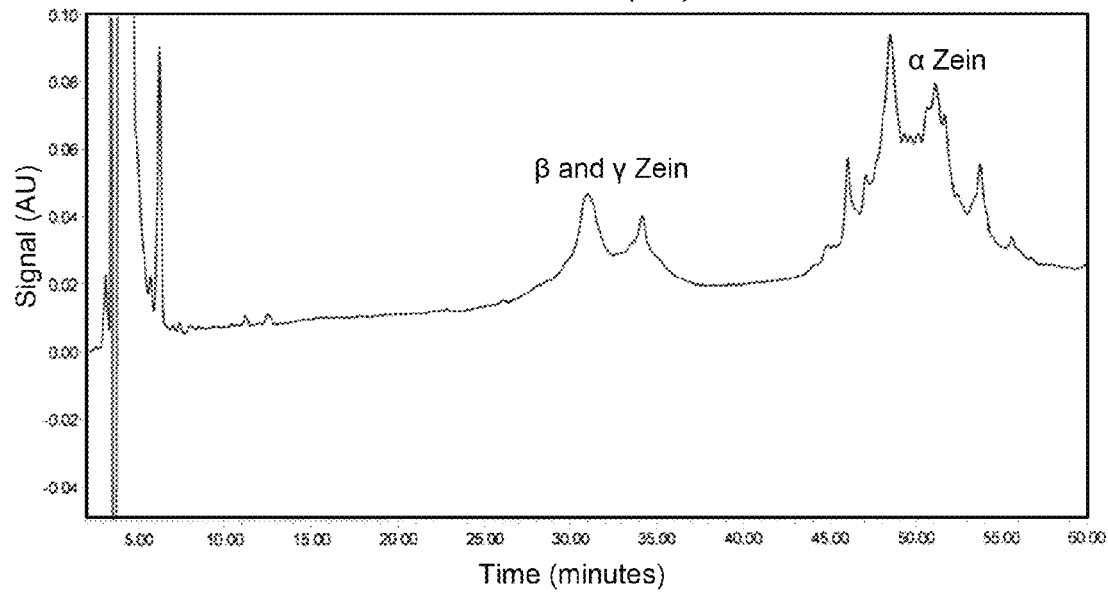
FIG. 12 is a table illustrating zein extraction yield from different starting materials, in accordance with some embodiments.
FIG. 13 is an example chromatogram of zein composition extracted from high protein dried distillers grain with an extraction agent, in accordance with some embodiments.

According to a series of examples, zein composition was extracted from different starting materials (beer, wet cake, and DDG) from the different ethanol processes (cooked starch fermentation, raw starch fermentation, and endosperm raw starch fermentation) to compare the zein yields. Zein was extracted using 70 percent ethanol in water with 3.5 percent sodium hydroxide (based on the dry solids of the starting material) at 70 degrees Celsius for 30 minutes. FIG. 12 is a table illustrating the example zein extraction yields. Extracting from DDG (from raw starch fermentation) recovers more zein than does extracting from DDG from a "cooked starch" fermentation process (shown as "conventional fermentation"). The combination of corn fractionation and raw starch fermentation provides better extraction efficiencies (at best partially explained by the higher protein content of DDG HP).

Further, zein compositions were extracted from Corn Gluten Meal (CGM) and High Protein Dried Distillers Grain (DDG HP) under a single extraction with sodium hydroxide, as well as by a double extraction as outlined above in reference to FIG. 4. The single extraction was performed using 70 percent ethanol in water with 3.5 percent sodium hydroxide (based on the dry solids of the starting material) at 70 degrees Celsius for 30 minutes. Double extraction consisted of an initial extraction using 70 percent ethanol in water at 70 degrees Celsius for 30 minutes, and a re-extraction on the pre-extracted solids using 70 percent ethanol in water with 3.5 percent sodium hydroxide (based on the dry solids of the starting material) at 70 degrees Celsius for 30 minutes. FIGS. 13-18 provide example HPLC chromatograms of zein compositions extracted under these conditions at laboratory scale.

FIG. 13 illustrates the zein HPLC chromatogram for DDG HP after a single extraction (with extraction agent). Shown are alpha-zein (α zein), beta-zein (β zein) and gamma-zein (γ zein). The peaks for beta and gamma-zein did not completely separate using this technique, and the relative amounts of beta- and gamma- are reported as a total sum of both types of zein. Note that inclusion of an extraction agent, such as an alkali like sodium hydroxide, enables access by the solvent to the beta zein (β zein) and gamma zein (γ zein).

Figure 14:
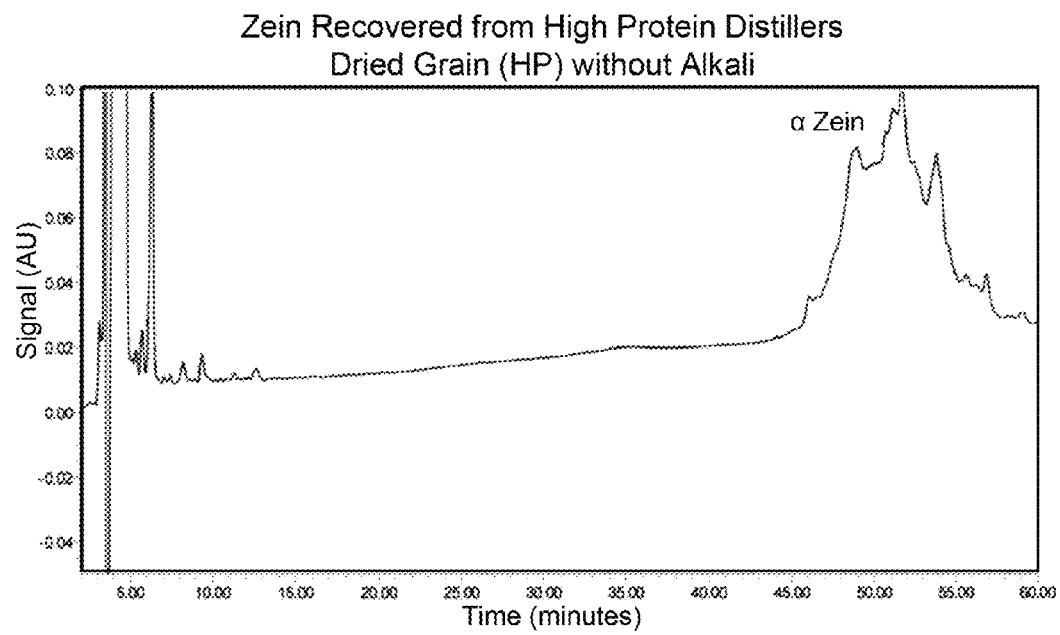
FIG. 14 is an example chromatogram of zein composition extracted from high protein dried distillers grain without an extraction agent, in accordance with some embodiments.

In contrast, FIG. 14 illustrates the HPLC chromatogram for zein recovered from DDG HP after the initial extraction of a double extraction procedure. This extraction is identical to the previous extraction except that no extraction agent is utilized. A peak for the recovered alpha-zein may be clearly seen; however, without an alkali (or other extraction agent) the yields of beta- and gamma-zein are all but nonexistent.

Figure 15:
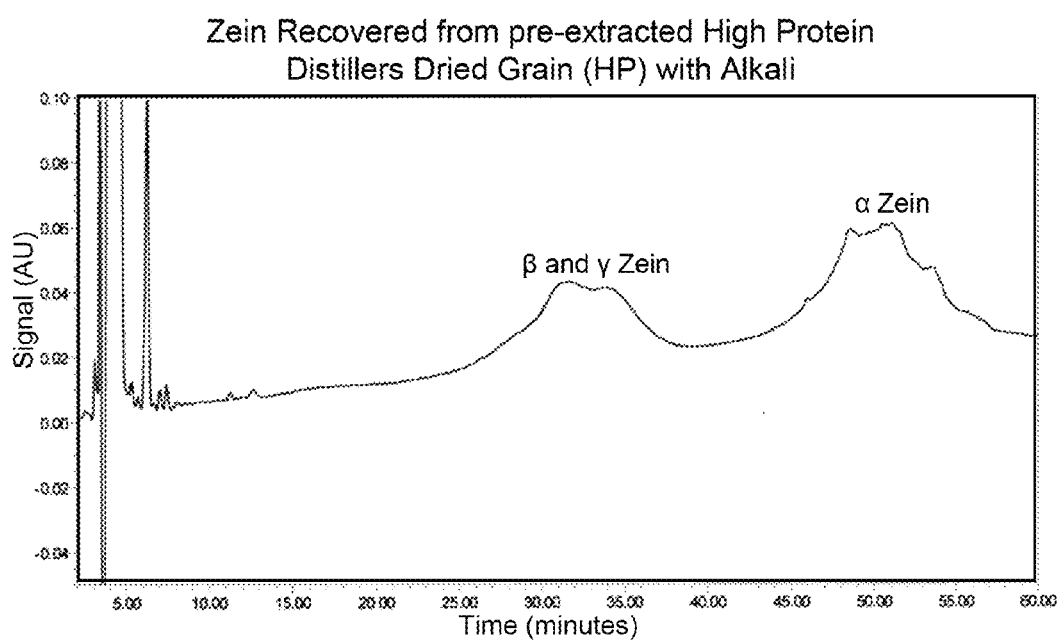
FIG. 15 is an example chromatogram of zein composition extracted from pre-extracted high protein dried distillers grain with an extraction agent, in accordance with some embodiments.

After the initial extraction of the DDG HP, the resulting solids (pre-extracted DDG HP) may be subject to a re-extraction. Re-extraction is performed with the use of an extraction agent, such as sodium hydroxide. The HPLC chromatogram for the zein recovered from pre-extracted DDG HP after a re-extraction is illustrated at FIG. 15. Shown are alpha-zein (α zein), beta-zein (β zein) and gamma-zein (γ zein). Again, the peaks for beta- and gamma-zein did not completely separate using this technique, and the relative amounts of beta- and gamma- are reported as a total sum of both types of zein. Of note, is that the relative amounts of beta- and gamma-zein are much higher after re-extraction from a pre-extracted DDG HP.

Further, relative amounts of alpha-zein (α zein), beta-zein (β zein) and gamma-zein (γ zein) may be further controlled through routine manipulation of the temperature, timing and solvent concentration used for the initial extraction, and the subsequent re-extraction. Further, it may be possible to further increase the relative content of the beta and gamma-zein through the use of more than one initial wash without an extraction agent.

Figure 16:
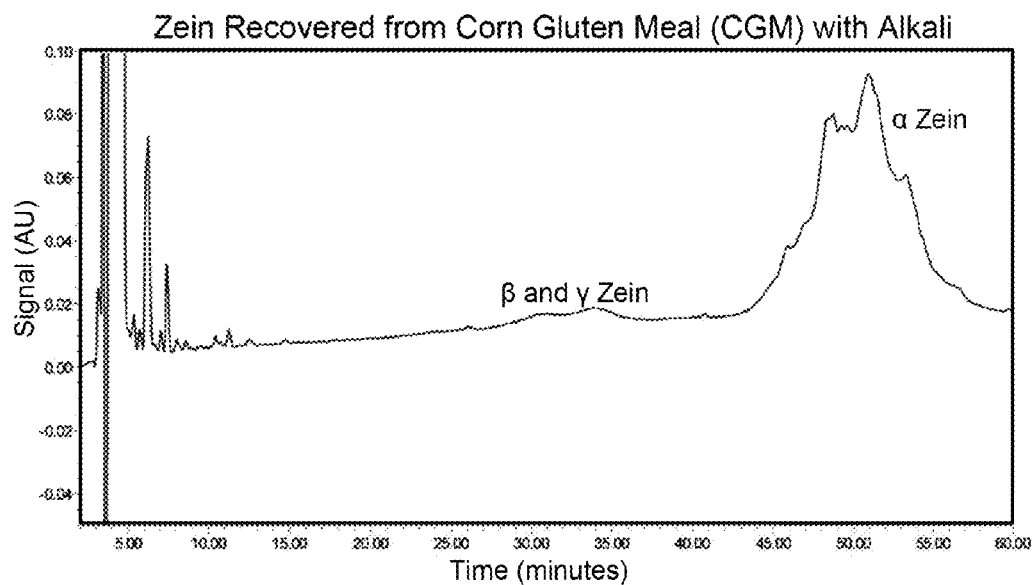
FIG. 16 is an example chromatogram of zein composition extracted from corn gluten meal with an extraction agent, in accordance with some embodiments.

A similar set of examples were generated using Corn Gluten Meal (CGM) as a starting material. FIG. 16 illustrates the zein HPLC chromatogram for CGM after a single extraction (with extraction agent). Shown are alpha-zein (α zein), beta-zein (β zein) and gamma-zein (γ zein). Unlike DDG HP, even with the inclusion of an alkali, the extraction still yields a predominantly alpha-zein product.

Figure 17:
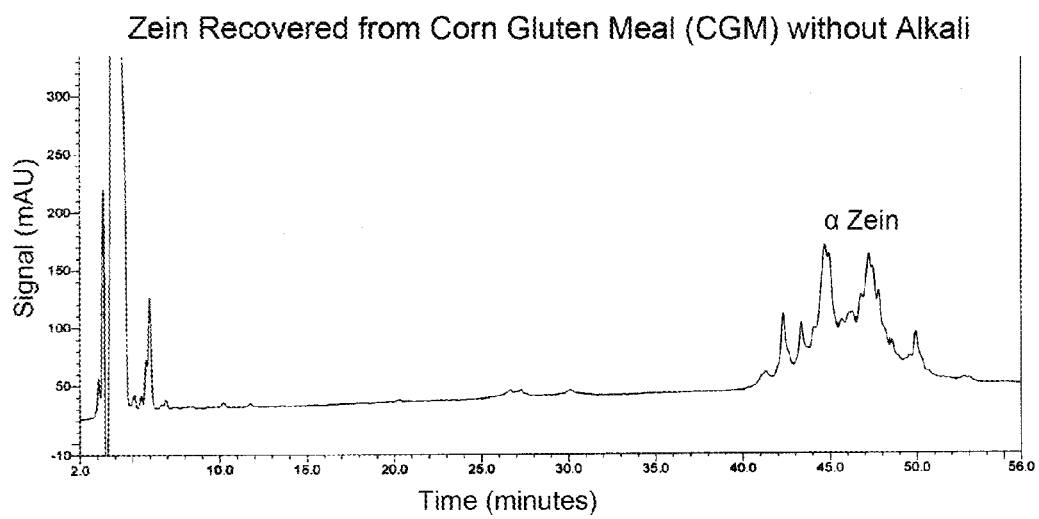
FIG. 17 is an example chromatogram of zein composition extracted from corn gluten meal without an extraction agent, in accordance with some embodiments.
Figures 18, 19:
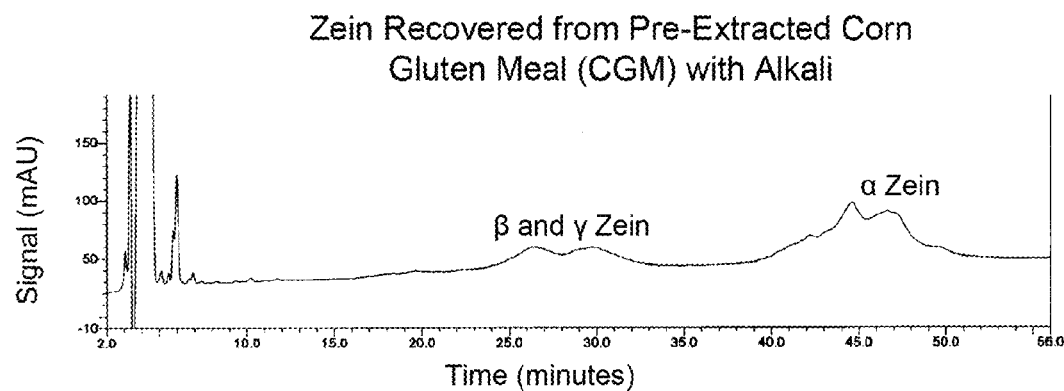
FIG. 18 is an example chromatogram of zein composition extracted from pre-extracted corn gluten meal with an extraction agent, in accordance with some embodiments.
FIG. 19 is a table for composition of zein from data generated from experimental extractions, in accordance with some embodiments.

FIG. 17 illustrates the zein HPLC chromatogram for zein recovered from CGM after the initial extraction of a double extraction procedure. Here no alkali is utilized, with almost imperceptible extraction of beta-zein (β zein) and gamma-zein (γ zein). Lastly, FIG. 18 illustrates the HPLC chromatogram for zein recovered from re-extraction of pre-extracted CGM with the use of an extraction agent. Here the relative amounts of beta- and gamma-zein are much higher after re-extraction from a pre-extracted GCM than under other extraction techniques. The peaks for beta and gamma-zein did not completely separate using this technique, and the relative amounts of beta- and gamma- are reported as a total sum of both types of zein.

FIG. 19 provides a table for compositions of the zein products recovered from experiments as outlined in relation to FIGS. 13-18. The alpha-, beta-, and gamma-zein composition of zein was obtained by analysis of RP-HPLC chromatograms of zein. The starting material for these experiments is illustrated in the first column. Starting material includes DDG HP, pre-extracted DDG HP, CGM, and pre-extracted CGM. The data is from experimental extractions using solvent (ethanol) with ("Yes") or without ("No") sodium hydroxide (NaOH) as an extraction agent. For DDG HP extractions with sodium hydroxide the average alpha-zein content is 77-88%, whereas beta- and gamma-zein content averaged 12-23%. Fat content was measured at 1.5% and 91% of the dry material is protein. In contrast, when the extraction is performed on DDG HP without sodium hydroxide, the composition was found to be almost entirely alpha-zein. Protein is similar at 86.5% and fat is increased to 7%. If the solids from this extraction (pre-extraction DDG HP) are re-extracted using sodium hydroxide, and even higher content of beta- and gamma-zein is realized at 41%. Alpha-zein is reduced to 59%, and almost all of the product of the re-extraction is protein at 92.3%.

The trends for extractions on CGM differ slightly. Particularly, when CGM is used as a starting material, the inclusion of sodium hydroxide does not appear to dramatically affect yields of beta- and gamma-zein. In fact, beta- and gamma-zein yields were 2.9 and 3.3 respectively for extractions with and without sodium hydroxide. High protein and low fat values are also seen for these samples. However, the second extraction of a pre-extracted CGM, with the inclusion of sodium hydroxide, yields a much higher value for beta and gamma zein content at 28.8%. Alpha zein is likewise reduced to 71.2%. Fat remains very low and protein content very high for these extractions.

In accordance with various embodiments, the concentrations of the various proteins of zein may be altered by processing to recover, within the available range, a zein intended to have a composition more specifically applicable to the intended commercial uses (such as by increasing the beta- and gamma-zein percentage to allow for more usage in strength-requiring applications).

Conventional zein extraction methods utilize seventy percent aqueous ethanol to extract zein. In some embodiments it is further possible to provide methods where the ethanol concentration is increased after extraction, such as to ninety percent. As a result of increasing the percentage of ethanol, more beta-zein and gamma-zein can precipitate out of the zein solution. Zein that has already been recovered by the conventional zein extraction can be redissolved in ninety percent ethanol. The zein that remains undissolved is high in beta-zein and gamma-zein. Both described methods can produce a zein fraction that contain more than 50% beta-zein and gamma-zein. In such a way even greater control over zein content may be established.

Yields of recovered zein depend on time, temperature, particle size, and percent aqueous alcohol used for the extraction. As noted, sodium hydroxide, or other extraction agent, can also be added to the solvent to increase the zein yields. Using sodium hydroxide (e.g., as an extraction agent) in the solvent also changes the solubility of beta and gamma zein and enables the extraction of beta and gamma zein. Other extraction agents may also be used, such as another alkali hydroxide (e.g., potassium hydroxide), an acid (hydrochloric acid or sulfuric acid), or a sulfite (e.g., sodium sulfite, sodium bisulfate or sodium metabisulfite). The relative volumes of ethanol, extraction agent, and starting material will change based on the moisture content of the starting material and targeted ethanol concentration.

In some cases, zein recovery is improved by extracting at 50 degrees Celsius or higher and by the addition of 3.5 percent sodium hydroxide or another reducing agent to the aqueous alcohol. By increasing the pH of the extracting solvent using sodium hydroxide, zein recovery tends to increase. Decreasing pH decreases the material recovered to a minim at about pH of 5, further lowering the pH below 5 increases the amount of zein recovered, but not to the same extent as increasing the pH. Decreasing the pH also lowers protein in the recovered material. Lowering the pH also decrease the amount of beta-zein and gamma-zein recovered. Decreasing the pH to below 5.5 reduces the amount of beta-zein and gamma-zein in the recovered material to 0-5%.

The terms "dried distillers grains," "DDG," "dried distillers grains with solubles," "DDGS," "grains," "granular material," "pelletized material" or the like can refer to particulate matter. Although many types of biomass may be fermented in an alcohol plant producing various types of particulate products to be transported to other locations, a corn-based ethanol plant producing dried distillers' grains is discussed throughout this application for illustrative purposes of material properties and operational aspects for embodiments.

The word "exemplary" is used to mean serving as an example, instance, or illustration. Any aspect or design described as "exemplary" is not necessarily to be construed as preferred or advantageous over other aspects or designs, nor is it meant to preclude equivalent exemplary structures and techniques known to those of ordinary skill in the art. Rather, use of the word exemplary is intended to present concepts in a concrete fashion, and the disclosed subject matter is not limited by such examples.

The term "or" is intended to mean an inclusive "or" rather than an exclusive "or." To the extent that the terms "comprises," "has," "contains," and other similar words are used in either the detailed description or the claims, for the avoidance of doubt, such terms are intended to be inclusive in a manner similar to the term "comprising" as an open transition word without precluding any additional or other elements.

In view of the exemplary apparatus and methods, methodologies that may be implemented in accordance with the disclosed subject matter will be better appreciated with reference to the flowcharts of the various figures. While for purposes of simplicity of explanation, the methodologies were shown and described as a series of blocks, it is to be understood and appreciated that the claimed subject matter is not limited by the order of the blocks, as some blocks may occur in different orders and/or concurrently with other blocks from what is depicted and described. Moreover, not all illustrated blocks may be required to implement the methodologies.

It is important to note that the construction and arrangement of the elements of the disclosed subject matter as described in this application and as shown in the figures is illustrative only. Although some embodiments have been described in detail in this disclosure, those skilled in the art who review this disclosure will readily appreciate that many modifications are possible (e.g. variations in size, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed, the operation of the interfaces may be reversed or otherwise varied, the length or width of the structures and/or members or connectors or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures and combinations. Accordingly, all such modifications are intended to be comprised within the scope of the disclosed subject matter. Other substitutions, modifications, changes and omissions may be made in the design, operating conditions and arrangement of the exemplary embodiments without departing from the spirit of the present inventions.

What is claimed is:

1. An extracted zein composition comprising beta-zein and gamma-zein in a combined percentage of from about 12 percent to about 60 percent by weight of zein within the extracted zein composition by dry weight.

2. The zein composition of claim 1, wherein the average cysteine amino acid residues per zein protein molecule in the composition is 4 or greater.

3. The zein composition of claim 1, wherein the zein composition comprises by dry weight basis:
   a protein component of at least 70 percent by weight of the zein composition, wherein the protein component substantially comprises zein; and
   a fat component of no more than 10 percent by weight of the zein composition.

4. The zein composition of claim 1, wherein the zein composition comprises alpha zein in a percentage of no more than 80 percent by weight of zein within the zein composition by dry weight.

5. The zein composition of claim 1, wherein the zein composition is produced from a fermentation product produced from a feedstock in a biorefining system.

6. The zein composition of claim 5, wherein the zein composition is produced from a fermentation product produced from a feedstock in a biorefining system comprising the steps of:
   processing the feedstock into a starch containing component;
   preparing the starch containing component into a fermentable component for fermentation;
   fermenting at least a portion of the fermentable component into the fermentation product; and
   producing the zein composition from the fermentation product.

7. The zein composition of claim 6, wherein the fermentation product comprises beer and the zein composition is extracted from the beer.

8. The zein composition of claim 6, wherein the fermentation product comprises ethanol and stillage, and further wherein the stillage comprises wet cake.

9. The zein composition of claim 5, wherein the biorefining system comprises a distillation system to which the fermentation product is supplied and the step of extracting the zein composition is conducted after the fermentation product has been supplied to the distillation system.

10. The zein composition of claim 5, wherein the step of producing the zein composition comprises the step of applying a solvent composition to the fermentation product and solids in the fermentation product are separated using the solvent composition.

11. The zein composition of claim 10, wherein the fermentation product comprises fermentation solids and the step of producing the zein composition further comprises:
   milling the fermentation solids;
   supplying the milled fermentation solids to a first vessel;
   treating the milled fermentation solids with a first solvent composition in the first vessel;
   separating a first batch of dissolved solids in the fermentation product with the first solvent composition;
   supplying the fermentation solids to a second vessel;
   treating the fermentation solids with a second solvent composition in the second vessel, wherein the second solvent composition includes an extraction agent; and
   separating a second batch of dissolved solids in the fermentation product with the second solvent composition.

12. The zein composition of claim 10, wherein the fermentation solids comprise meal.

13. The zein composition of claim 11, wherein the fermentation solids comprise dried distillers grains.

14. The zein composition of claim 6, wherein the feedstock is corn and the step of processing the feedstock comprises fractionating the corn into endosperm, germ and fiber and the starch containing component comprises endosperm substantially free of germ and fiber.

15. The zein composition of claim 6, wherein the step of preparing the starch containing component into the fermentable component comprises liquefaction.

16. The zein composition of claim 6, wherein the step of preparing the starch containing component into a fermentable component comprises raw starch hydrolysis.

17. The zein composition of claim 11, wherein the extraction agent comprises an acid.

18. The zein composition of claim 11, wherein the extraction agent comprises an alkali.

19. The zein composition of claim 18, wherein the extraction agent comprises sodium hydroxide.

20. The zein composition of claim 11, wherein the extraction agent comprises a sulfite.

21. The zein composition of claim 20, wherein the extraction agent comprises sodium metabisulfite.

22. The zein composition of claim 18, wherein the extraction agent comprises potassium hydroxide.

23. The zein composition of claim 11, wherein the extraction agent comprises thiol.

24. The zein composition of claim 23, wherein the extraction agent comprises 2-mercaptoethanol.

25. The zein composition of claim 6, further comprising the step of drying the zein composition and wherein the zein composition has been produced without raising the temperature of the zein composition above about 130° C.

* * * * *